(12) United States Patent
Williams

(10) Patent No.: US 7,655,411 B2
(45) Date of Patent: *Feb. 2, 2010

(54) THROMBOSPONDIN FRAGMENTS AND BINDING AGENTS IN THE DETECTION, DIAGNOSIS AND EVALUATION OF CANCER

(75) Inventor: Kevin J. Williams, Wynnewood, PA (US)

(73) Assignee: W2 Holdings, Inc., Philadelphia, PA (US)

( * ) Notice: Subject to any disclaimer, the term of this patent is extended or adjusted under 35 U.S.C. 154(b) by 1011 days.

This patent is subject to a terminal disclaimer.

(21) Appl. No.: 10/419,462

(22) Filed: Apr. 21, 2003

(65) Prior Publication Data

US 2004/0053392 A1 Mar. 18, 2004

Related U.S. Application Data

(60) Provisional application No. 60/405,494, filed on Aug. 23, 2002.

(51) Int. Cl.
| | |
|---|---|
| G01N 33/53 | (2006.01) |
| C12Q 1/00 | (2006.01) |
| G01N 33/48 | (2006.01) |
| G01N 33/00 | (2006.01) |
| G01N 1/00 | (2006.01) |
| G01N 1/18 | (2006.01) |

(52) U.S. Cl. ............... 435/7.1; 435/4; 436/63; 436/64; 436/86; 436/174; 436/177

(58) Field of Classification Search ............... 435/4, 435/7.1; 436/63, 64, 86, 174, 177
See application file for complete search history.

(56) References Cited

U.S. PATENT DOCUMENTS

| | | | |
|---|---|---|---|
| 4,610,960 | A | 9/1986 | Mosher |
| 4,820,505 | A | 4/1989 | Ginsberg et al. |
| 5,192,744 | A | 3/1993 | Bouck et al. |
| 5,256,538 | A | 10/1993 | Aiken et al. |
| 5,654,277 | A | 8/1997 | Eyal et al. |
| 5,686,583 | A | 11/1997 | Bosslet et al. |
| 5,750,502 | A | 5/1998 | Jessell et al. |
| 5,753,517 | A | 5/1998 | Brooks et al. |
| 5,770,563 | A | 6/1998 | Roberts |
| 5,840,507 | A | 11/1998 | Fruehauf |
| 5,840,692 | A | 11/1998 | Deutch et al. |
| 6,051,549 | A | 4/2000 | Roberts et al. |
| 6,239,110 | B1 | 5/2001 | Eyal et al. |
| 6,339,062 | B1 | 1/2002 | Williams et al. |
| 2001/0041670 | A1 | 11/2001 | Simantov et al. |
| 2002/0197697 | A1 | 12/2002 | Abdelouahed et al. |
| 2003/0119074 | A1 | 6/2003 | Jackowski |
| 2003/0166017 | A1 * | 9/2003 | McCarthy ............ 435/7.21 |
| 2003/0180295 | A1 | 9/2003 | Tuszynski et al. |

FOREIGN PATENT DOCUMENTS

| | | | |
|---|---|---|---|
| WO | WO9807035 | * | 2/1998 |
| WO | WO 01/05968 | | 1/2001 |

OTHER PUBLICATIONS

Lawler JW et al. Isolation and characterization of a high molecular weight glycoprotein from human blood platelets. J. Biol. Chem., 1978. 253(23):8609-8616. (Abstract only).
Wallinder L et al. Rapid removal to the liver of intravenously injected lipoprotein lipase. Biochem. Biophys. Acta, Oct. 26, 1979; 575(1):166-173. (Abstract only).
Margossian SS et al. Physical characterization of platelet thrombospondin. J. Biol. Chem., 1981. 256(14):7495-7500, (Abstract only).
Saglio SD et al. Use of a radioimmunoassay to quantify thrombospondin. Blood, Jan. 1982; 59(1):162-166. (Abstract only).
Mosher DF et al. Synthesis and secretion of thrombospondin by cultured human endothelial cells. J. Cell Biol., 1982. 93(2):343-348.
Dawes J et al. A radioimmunoassay for thrombospondin, used in a comparative study of thrombospondin, beta-thromboglobulin and platelet factor 4 in healthy volunteers. Thromb. Res., Mar. 15, 1983; 29:569-581.
Jaffe EA et al. Cultured human fibroblasts synthesize and secrete thrombospondin and incorporate it into extracellular matrix. Proc. Natl. Acad. Sci., USA, Feb. 1983; 80(4):998-1002.
Prowse CV et al. A comparative study using immunological and biological assay of the haemostatic responses to DDAVP infusion venous occlusion and exercise in normal men. Thromb. Haemost., Feb. 28, 1984; 51(1):110-114. (Abstract only).
Mumby SM et al. Interactions of thrombospondin with extracellular matrix proteins: selective binding to type V collagen. J. Cell Biol., 1984. 98(2):646-652. (Abstract only).
Coligan, JE and Slayter HS. Structure of thrombospondin. J. Biol. Chem., 1984. 259:3944-3948.
Dixit VM et al. Isolation and characterization of a heparin-binding domain from the amino terminus of platelet thrombospondin. J Biol Chem, 1984. 259:10100-10105. (Abstract only).
Lane DA et al. Detection of enhanced in vivo platelet alpha-granule release in different patient groups—comparison of beta-thromboglobulin, platelet factor 4 and thrombospondin assays. Thromb. Haemost., Oct. 31, 1984; 52(2):183-187. (Abstract only).
Lahav J et al. Thrombospondin interactions with fibronectin and fibrinogen. Mutual inhibition in binding. Eur. J. Biochem., Nov. 15, 1984; 145(1):151-156. (Abstract only).
Silverstein RL et al. Complex formation of platelet thrombospondin with plasminogen. Modulation of activation by tissue activator. J. Clin. Invest., Nov. 1984; 74(5):1625-1633. (Abstract only).

(Continued)

Primary Examiner—Alana M Harris
(74) Attorney, Agent, or Firm—Caesar, Rivise, Bernstein, Cohen & Pokotilow, Ltd.

(57) ABSTRACT

The invention relates to thrombospondin fragments found in plasma, their use or use of portions thereof in diagnostic methods, as method calibrators, method indicators, and as immunogens, and as analytes for methods with substantial clinical utility; and their detection in plasma or other bodily fluids for purpose of diagnostic methods, especially for cancer.

12 Claims, 4 Drawing Sheets

OTHER PUBLICATIONS

Lawler J et al. The structure of human platelet thrombospondin. J. Biol. Chem., 1985. 260:3762-3772.

Roberts DD et al. Thrombospondin binds falciparum malaria parasitized erythrocytes and may mediate cytoadherence. Nature, 1985. 318(6041):64-66. (Abstract only).

Jaffe EA et al. Monocytes and macrophages synthesize and secrete thrombospondin. Blood, Jan. 1985; 65(1):79-84. (Abstract only).

Dixit VM et al. Effects of anti-thrombospondin monoclonal antibodies on the agglutination of erythrocytes and fixed, activated platelets by purified thrombospondin. Biochemistry, Jul. 30, 1985; 24(16):4270-4275.

Silverstein RL et al. Activation of immobilized plasminogen by tissue activator. Multimolecular complex formation. J. Biol. Chem., 1985. 260(18):10346-10352.

Galvin NJ et al. Mapping of epitopes for monoclonal antibodies against human platelet thrombospondin with electon microscopy and high sensitivity amino acid sequencing. J. Cell Biol., 1985. 101(4):1434-1441.

Trzeciak MC et al. Plasma thrombospondin in patients with chronic renal failure, liver disease and splenectomy. Thromb. Res., Oct. 1, 1985; 40(1):121-128. (Abstract only).

Tuszynski GP et al. The interaction of human platelet thrombospondin with fibrinogen. Thrombospondin purification and specificity of interaction. J. Biol. Chem., 1985. 260(22):12240-12245.

Miller WR et al. Platelet-associated proteins in human breast cyst fluids. Clin. Chim. Acta, Oct. 31, 1985; 152(1-2):37-42. (Abstract only).

Switalska HI et al. Radioimmunoassay of human platelet thrombospondin: different patterns of thrombospondin and beta-thromboglobulin antigen secretion and clearance from the circulation. J. Lab. Clin. Med., Dec. 1985; 106(6):690-700. (Abstract only).

Kaplan KL et al. Plasma levels of platelet secretory proteins. Crit. Rev. Oncol. Hematol., 1986. 5(3):235-255. (Abstract only).

Dixit VM et al. Monoclonal antibodies that recognize calcium-dependent structures of human thrombospondin. Characterization and mapping of their epitopes. J. Biol. Chem., 1986, 261(4):1962-1968.

Wolff R et al. Interaction of thrombospondin with resting and stimulated human platelets. J. Biol. Chem., 1986. 261(15):6840-6846.

Kao KJ et al. A monoclonal antibody-based enzyme-linked immunosorbent assay for quantitation of plasma thrombospondin. Am. J. Clin. Pathol., Sep. 1986; 86(3):317-323. (Abstract only).

Frazier WA. Thrombospondin: a modular adhesive glycoprotein of platelets and nucleated cell. J. Cell Biol., 1987. 105(2):625-632.

Asch AS et al. Isolation of the thrombospondin membrane receptor. J. Clin. Invest., Apr. 1987; 79:1054-1076. (Abstract only).

Galvin NJ et al. Interaction of human thrombospondin with types I-V collagen: direct binding and electron microscopy. J. Cell Biol., 1987. 104(5):1413-1422. (Abstract only).

Dardik R et al. The structure of endothelial cell thrombospondin. Characterization of the heparin-binding domains. Eur. J. Biochem., Oct. 15, 1987; 168(2):347-355. (Abstract only).

McCrohan MB et al. Plasma thrombospondin as an indicator of intravascular platelet activation in patients with vasculitis. Thromb. Haemost., Oct. 28, 1987; 58(3):850-852. (Abstract only).

Legrand C et al. Use of a monoclonal antibody to measure the surface expression of thrombospondin following platelet activation. Eur. J. Biochem., Jan. 15, 1988; 171(1-2):393-399. (Abstract only).

Majack RA et al. Cell surface thrombospondin is functionally essential for vascular smooth muscle cell proliferation. J. Cell Biol. Feb. 1988; 106:415-422.

Dawes J et al. Do extra-platelet sources contribute to the plasma level of thrombospondin? Thromb. Haemost., Apr. 8, 1988; 59(2):273-276. (Abstract only).

Clezardin P et al. Complex formation of human thrombospondin with osteonectin. Eur. J. Biochem., Aug. 1, 1988; 175:275-284. (Abstract only).

Asch AS and Nachman RL. Thrombospondin: phenomenology to function. Prog. Hemost. Thromb., 1989. 9:157-176. (Abstract only).

Gehron-Robey P et al. Thrombospondin is an osteoblast-derived component of mineralized extracellular matrix. J. Cell Biol., 1989. 108:719-727.

Cardin AD and Weintraub HJ. Molecular modeling of protein-glycosaminoglycan interactions. Arteriosclerosis, Jan.-Feb. 1989; 9(1):21-32. (Abstract only).

Bacon-Baguley T et al. Thrombospondin binding to specific sequences within the Aα- and Bβ-chains of fibrinogen. J. Biol. Chem., 1990. 265(4):2317-23.

Silverstein RL et al. Thrombospondin forms complexes with single-chain and two-chain forms of urokinase. J. Biol. Chem., 1990. 265(19):11289-11294. (Abstract only).

Good DJ et al. A tumor suppressor-dependent inhibitor of angiogenesis is immunologically and functionally indistinguishable from a fragment of thrombospondin. Proc. Natl. Acad. Sci., USA, Sep. 1990; 87:6624-6628.

Dardik R et al. Cell-binding domain of endothelial cell thrombospondin: localization to the 70kDa core fragment and determination of binding characteristics. Biochemistry, Sep. 24, 1991; 30(38):9378-9386.

Sage EH and Bornstein P. Extracellular proteins that modulate cell-matrix interactions. SPARC, tenascin, and thrombospondin. J. Biol. Chem., 1991. 266(23):14831-14834.

Frazier WA. Thrombospondins. Current. Opin. Cell Biol., 1991. 3(5): 792-799. (Abstract only).

Tuszynski GP et al. Biological activities of peptides and peptide analogues derived from common sequences present in thrombospondin, properdin, and malarial proteins. J. Cell Biol., 1992. 116(1):209-217.

Lawler J et al. Expression and mutagenesis of thrombospondin. Biochemistry, Feb. 4, 1992; 31(4):1173-1180.

Prater CA et al. The properdin-like type I repeats of human thrombospondin contain a cell attachment site. J. Cell Biol., 1991. 112(5):1031-1040.

Osterhout DJ et al. Thrombospondin promotes process outgrowth in neurons from the peripheral and central nervous systems. Devel. Biol, 1992. 150(2):256-265. (Abstract only).

Tuszynski GP et al. Thrombospondin levels in patients with malignancy. Thromb. Haemost., 1992. 67(6):607-611. (Abstract only).

Kosfeld MD et al. Identification of active peptide sequences in the carboxyl-terminal cell binding domain of human thrombospondin-1. J. Biol. Chem., 1992. 267(23):16230-16236.

Zafar RS et al. Localization of two binding domains for thrombospondin within fibronectin. Arch. Biochem. Biophys., Sep. 1992; 297(2):271-276. (Abstract only).

Soga T et al. Analysis of adhesive proteins on the surface of platelets from the patients with lung cancer: studies in histological type and clinical stage. Rinsho Ketsueki, Sep. 1992; 33(9):1121-1127. [Article in Japanese] (English Abstract only).

Takagi T et al. A single chain 19-kDa fragment from bovine thrombospondin binds to type V collagen and heparin. J. Biol. Chem., 1993. 268(21):15544-15549.

Murphy-Ullrich JE et al. Heparin-binding peptides from thrombospondins 1 and 2 contain focal adhesion-labilizing activity. J. Biol. Chem., 1993. 268(35): 26784-26789. (Abstract only).

Lawler J et al. Identification and characterization of thrombospondin-4, a new member of the thrombospondin gene family. J. Cell Biol., 1993. 120(4):1059-1067.

Sipes JM et al. Inhibition of fibronectin binding and fibronectin-mediated cell adhesion to collagen by a peptide from the second type I repeat of thrombospondin. J. Cell Biol., 1993. 121(2):469-477.

Tolsma et al. Peptides derived from two separate domains of the matrix protein thrombospondin-1 have anti-angiogenic activity. J. Cell Biol., 1993. 122(2):497-511.

Huang SW et al. The relationship between plasma thrombospondin level and the clinical course of atopic dermatitis. Allergy Proc., Sep.-Oct. 1993; 14(5):357-361. (Abstract only).

Zammit A et al. Interaction of immobilised unfractionated and LMW heparins with proteins in whole human plasma. Thromb. Haemost., Dec. 20, 1993; 70(6):951-958. (Abstract only).

Morandi V et al. Characterization of a novel monoclonal antibody (V58A4) raised against a recombinant NH2-terminal heparin-binding fragment of human endothelial cell thrombospondin. FEBS Lett, 1994. 346(2-3):156-160. (Abstract only).

Kanda S et al. Role of thrombospondin-1-derived peptide, 4N1K, in FGF-2-induced angiogenesis. Exp. Cell Res., 1999. 252(2):262-272.

Panetti TS et al. Interaction of recombinant procollagen and properdin modules of thrombospondin-1 with heparin and fibrinogen/fibrin. J. Biol. Chem., 1999. 274(1):430-437.

Roth JJ et al. Thrombospondin 1 and its specific cysteine-serine-valine-threonine-cysteine-cycline receptor in fetal wounds. Ann. Plast. Surg., May 1999; 42(5):553-563. (Abstract only).

Altun B et al. Thrombopoietin and thrombospondin in renal allograft recipients. Blood Coagul. Fibrinolysis, Jul. 1999; 10(5):233-237. (Abstract only).

Krutzsch HC et al. Identification of an α(3)β(1) integrin recognition sequence in thrombospondin-1. J. Biol. Chem., 1999. 274(34):24080-24086.

Nomura S et al. Relationship between platelet activation and cytokines in systemic inflammatory response syndrome patients with hematological malignancies. Thromb. Res., Sep. 1, 1999; 95:205-213.

Michelson AD and Furman MI. Laboratory markers of platelet activation and their clinical significance. Curr. Opin. Hematol., Sep. 1999; 6(5):342-348, Abstract only.

Chen et al. Cartilage oligomeric matrix protein is a calcium-binding protein, and a mutation in its type 3 repeats causes conformational changes. J. Biol. Chem., 2000. 275(34):26538-26544.

Voland C et al. Platelet-osteosarcoma cell interaction is mediated through a specific fibrinogen-binding sequence located within the N-terminal domain of thrombospondin 1. J. Bone Miner. Res., Feb. 2000; 15(2):361-368. (Abstract only).

Carron JA et al. A CD36-binding peptide from thrombospondin-1 can stimulate resportion by osteoclasts in vitro. Biochem. Biophys. Res. Commun., Apr. 21, 2000; 270(3):1124-1127. (Abstract only).

Hayden K et al. Radioimmunoassay for the measurement of thrombospondin in plasma and breast cyst fluid: validation and clinical application. Ann. Clin. Biochem., May 2000; 37 (Pt. 3):319-325.

Bergseth G et al. A novel enzyme immunoassay for plasma thrombospondin. Comparison with beta-thromboglobulin as platelet activation marker in vitro and in vivo. Thromb. Res., Jul. 1, 2000; 99:41-50.

Pini A and Bracci L. Phage display of antibody fragments. Curr. Protein Pept.Sci., Sep. 2000; 1(2):155-169. (Abstract only).

Rusnati M et al. Thrombospondin-l/HIV-1 TAT protein interaction: modulation of the biological activity of extracellular TAT. FASEB J. Oct. 2000; 14:1917-1930.

Bonnefoy a et al. A model of platelet aggregation involving multiple interactions of thrombospondin-1, fibrinogen and GPIIbIIIa receptor. J. Biol. Chem., 2001. 276(8):5605-5612.

Damas C et al. The 33-kDa platelet alpha-granule membrane protein (GMP-33) is an N-terminal proteolytic fragment of thrombospondin. Thromb. Haemost. Sep;86(3):887-893. (Abstract only).

Fraipont F et al. Thrombospondins and tumor angiongenesis. Trend Mol. Med., 2001. 7:401-407.

Hofsteenge J et al. C-mannosylation and O-fucosylation of the thrombospondin type 1 module. J. Biol. Chem., 2001. 276(9):6485-6498.

Hamaguchi N. et al. Aptamer beacons for the direct detection of proteins. Anal. Biochem., Jul. 15, 2001; 294(2):126-131. (Abstract only).

Nomura S et al. Function and clinical significance of platelet-derived microparticles. Int. J. Hematol., Dec. 2001; 74(4):397-404. (Abstract only).

Qian MD et al. Anti GPVI human antibodies neutralizing collagen-induced platelet aggregation isolated from a recombinant phage display library. Hum. Antibodies, 2002. 11(3):97-105. (Abstract only).

Zhang W et al. Production and characterization of human monoclonal anti-idiotype antibodies to ant-dsDNA antibodies. Lupus, 2002. 11(6):362-369. (Abstract only).

Asvadi P. et al. Expression and functional analysis of recombinant scFV and diabody fragments with specificity for human RhD. J. Mol. Recognit., 2002. 15:321-330. (Abstract only).

Rau D et al. Single-chain Fv antibody-alkaline phosphatase fusion proteins produced by one-step cloning as rapid detection tools for ELISA. J. Immunoassay Immunochem., 2002. 23(2):129-143. (Abstract only).

Flores-Flores C et al. Development of human antibody fragments directed towards synaptic acetylcholinesterase using a semi-synthetic phage display library. J. Neural. Transm. Suppl., 2002. 62:165-179. (Abstract only).

Stamey TA et al. Preoperative serum prostate specific antigen levels between 2 and 22 ng./ml. correlate poorly with post-radical prostatectomy cancer morphology: prostate specific antigen cure rates appear constant between 2 and 9 ng./ml. J Urology, Jan. 2002; 167(1):103-111. (Abstract only).

Baglia FA et al. Factor XI binding to the glycoprotein Ib-IX-V complex promotes factor XI activation by thrombin. J.Biol. Chem., 2002. 277(3):1662-8.

Rau D et al. Cloning, functional expression and kinetic characterization of pesticide-selective Fab fragment variants derived by molecular evolution of variable antibody genes. Anal. Bioanal. Chem., Jan. 2002; 372(2):261-267. (Abstract only).

Nathan S et al. Phage display of recombinant antibodies toward Burkholderia pseudomallei exotoxin. J. Biochem. Mol. Biol. Biophys., Feb. 2002; 6(1):45-53. (Abstract only).

Baek H et al. An improved helper phage system for efficient isolation of specific antibody molecules in phage display. Nucleic Acids Res., 2002. 30(5):e18.

Zhou B et al. Human antibodies against spores of the genus Bacillus: a model study for detection of and protection against anthrax and the bioterrorist threat. Proc. Natl. Acad. Sci., USA, 2002. Apr. 16;99(8):5241-5246. (Abstract only).

Gurney D et al. A reliable plasma marker of platelet activation: Does it exist? Am. J. Hematol., Jun. 2002; 70(2):139-144. (Abstract only).

Reich N. et al. Generation and characterization of human monoclonal scFv antibodies against Helicobacter pylori antigens. Infect. Immun., Aug. 2002; 70(8):4158-4164.

O'Connell D et al. Phage versus phagemid libraries for generation of human monoclonal antibodies. J. Mol. Biol., Aug. 2, 2002; 321(1):49-56. (Abstract only).

Lu D et al. Fab-scFv fusion protein: an efficient approach to production of bispecific antibody fragments. J. Immunol. Methods, Sep. 15, 2002; 267(2):213-226. (Abstract only).

Oelschlaeger P et al. Fluorophor-linked immunosorbent assay: a time- and cost-saving method for the characterization of antibody fragments using a fusion protein of a single-chain antibody fragment and enhanced green fluorescent protein. Anal. Biochem, Oct. 1, 2002; 309(1):27-34. (Abstract only).

Gao C et al. A method for the generation of combinatorial antibody libraries using pIX phage display. Proc. Natl. Acad. Sci., USA, Oct. 1, 2002; 99(20):12612-12616. (Abstract only).

Lee KJ et al. Phage-display selection of a human single-chain fv antibody highly specific for melanoma and breast cancer cells using a chemoenzymatically synthesized G(M3)-carbohydrate antigen. J. Am. Chem. Soc., Oct. 23, 2002; 124(42):12439-12446. (Abstract only).

Sinacola JR and Robinson AS. Rapid folding and polishing of single-chain antibodies from *Escherichia coli* inclusion bodies. Protein Expr. Purif:, Nov. 2002; 26(2):301-308. (Abstract only).

Epel M et al. A functional recombinant single-chain T cell receptor fragment capable of selectively targeting antigen-presenting cells. Cancer Immunol. Immunother., 2002. 51(10):565-573. (Abstract only).

Schlattner U et al. Isoenzyme-directed selection and characterization of anti-creatine kinase single chain Fv antibodies from a human phage display library. Biochem. Biophys. Acta, Dec. 12, 2002; 1579(2-3):124-132. (Abstract only).

Tuszynski GP et al., Methods of studying platelet-secreted proteins and the platelet cytoskeleton, Alan R. Liss, Inc., New York, p. 267-286, 1987.

Lawler J, et al., Thrombin and chymotrypsin interactions with thrombospondin. Ann NY Acad Sci. 1986; 485:273-87.

Walz, DA, et al.,Binding of thrombospondin to immobilized ligands: specific interaction with fibrinogen, plasminogen, histidine-rich glycoprotein, and fibronectin, Semin Thromb Hemost. 13(3): 317-025, 1987.

Adams, JC, et al.,The thrombospondin gene family, Springer-Verlag: New York, 1995, pp. 1-9, 11-56.

Vanguri, VK., Thrombospondin-1 binds to polyhistidine with high affinity and specifity, 2000 Biochem, p. 469-473.

Simantov, R., et al., Histidine-rich glycoprotein inhibits the antiangiogenic effect of thrombospondin-1, J. Clin. Invest. 2001, 107(1):45-52.

Trzeciak MC et al., Plasma thrombospondin in patients with chronic renal failure, liver disease and splenectomy. Thromb. Res. 1985; 40:121-128.

Ffrench P et al., Comparative evaluation of plasma thrombospondin beta-thromboglobulin and platelet factor 4 in acute myocardial infarction. Thromb. Res. 1985; 39:619-624.

Dawes J et al., A radioimmunoassay for thrombospondin, used in a comparative study of thrombospondin, beta-thromboglobulin and platelet factor 4 in healthy volunteers. Thromb. Res. 1983; 29: 569-581.

McCrohan MB et al., Plasma thrombospondin as an indicator of intravascular platelet activation in patients with vasculitis. Thromb Haemost. 1987; 58:850-852.

Huang S-W and Kao K-J, Plasma thrombospondin measurement in clinical practice. Internal Medicine for the Specialist. 1990. 11:52-70.

Tuszynski GP et al., Thrombospondin levels in patients with malignancy, Thromb Haemost 1992; 67:607-11.

Nathan FE et al., Plasma Thrombospondin levels in patients with gynecological malignancies. Cancer. 1994; 73:2853-8.

Yamashita Y et al., Plasma thrombospondin levels in patients with colorectal carcinoma. Cancer. 1998; 82:632-8.

Topol EJ et al., Single nucleotide polymorphisms in multiple novel thrombospondin genes may be associated with familial premature myocardial infarction. Circulation. 2001;104:2641-2644.

Baenziger NL, et al., A thrombin-sensitive protein of human platelet membranes. Proc. Natl. Acad. Sci. USA, 1971;68:240-253 (Abstract only).

Gullu IH et al., Plasma thrombospondin levels in patients with colorectal carcinoma. Cancer. 1998; 83:2043-45.

Asch AS, et al., Thrombospondin sequence moticf (CSVTCG) is responsible for CD36 binding. Biochem Biophys Res Commun. 1992; 182:1208-1217.

Clezardin P, et al.,Characterization of two murine monoclonal antibodies (P10, P12) directed against different determinants on human blood platelet thrombospondin. Eur J Bioch. 1986;154:95-102. (Abstract only).

Albo D, et al., Up-regulation of matrix metalloproteinase 9 by thrombospondin 1 in gastric cancer. J Surg Res. 2002;108:51-60.

Wight TN, et al., Light microscopic immunolocation of thrombospondin in human tissues. J Histochem Cytochem. 1985; 33:295-302. (Abstract only).

Serre CM, et al., Distribution of thrombospondin and integrin alpha V in DCIS, invasive ductal and lobular human breast carcinomas. Analysis by electron microscopy. Virchows Archiv. 1995;427:365-372. (Abstract only).

Matthias LJ, et al., Identification of monoclonal antibodies that recognize different disulfide bonded forms of thrombospondin 1. Biochim Biophys Acta. 1996; 1296: 138-144. (Abstract only).

Silverstein et al., Platelet thrombospondin forms a trimolecular complex with plasminogen and histidine-rich glycoprotein. J Clin Invest. 1985; 75:2065-73. (Abstract only).

Vastag B, Study concludes that moderate PSA levels are unrelated to prostate cancer outcomes. JAMA. 2002; 287:969-970.

Stancik R, et al.,Plasma levels of TPA, PAI-1, and thrombospondin in patients with systemic vasculitis. Clin App Throm Hemost. 1999;5:140-141.

Qian X et al., Expression of Thrombospondin-1 in Human Pancreatic Adenocarcinomas: role in matrix metalloproteinase-9 production. Pathology Oncology Res. 2001; 7:251-259.

Gladson CL. The role of TSP-1 and 2 in the biology of astrocytomas. NIH grant. 2002, No. 5R01CA097110-02. (Abstract Only).

Tuszynski, GP. Angiocidin, A new angiogenesis inhibitor. NIH grant. 2001. No. 7RO1CA088931-02. (Abstract only).

Tuszynski, GP. Antimetastatic effect of Thrombospondin derived from peptides. NIH grant. 2001. No. 1R41CA081822-01A2. (Abstract only).

Huang SW and Kao KJ, Use of thrombospondin level to predict the clinical course of atopic dermatitis associated with food hypersensitivity or skin infection. J Dermatol Sci. 1996; 11:59-63. (Abstract only).

Figure 1: Structural and functional domains of thrombospondin-1. 2002. http://research.bidmc.harvard.edu/Pathology/images/tspl.jpg.

Huang S-W et al., Plasma Thrombospondin levels in sheep with allergic asthma. Chest. 1996; 109: 1614-1617.

Aiken ML, Isolation and characterization bovine platelet thrombospondin (protein). Dissertation. Wayne State University. 1984. (Abstract only).

Rice AJ, et al. Thrombospondin 1 protein expression relates to good prognostic indices in ductal carcinoma of the breast. J Clin Pathol. 2002; 55:921-925. (Abstract only).

Goddard JC, et al., Reduced thrombospondin-1 at presentation predicts disease progression in superficial bladder cancer. Eur Urol. 2002; 42:464-468. (Abstract only).

Mascaux C, et al., Expression of thrombospondin in non-small cell lung cancer. Anticancer Res. 2002; 22:1273-1277. (Abstract only).

Qin LX, et al., The prognostic molecular markers in hepatocellular carcinoma. World J Gastroenterol. 2002; 8:385-392. (Abstract only).

Wakiyama T, et al., The localization of thrombospondin-1 (TSP-1), cysteine-serine-valine-threonine-cysteine-glycine (CSVTCG) TSP receptor, and matrix metalloproteinase-9 (MMP-9_in colorectal cancer. Histol Hostopathol. 2001; 16:345-351. (Abstract only).

Kuroi K, et al., Circulating angiogenesis regulators in cancer patients. Int J Biomarkers. 2001; 16: 5-26. (Abstract only).

Kasper HU, et al., Expression of thrombospondin-1 in pancreatic carcinoma: correlation with microvessel density. Virchows Arch. 2001;438;116-120. (Abstract only).

Tuszynski GP, et al., The role of thrombospondin-1 in tumor progression and angiogenesis. Bioessays. 1996; 18: 71-76. (Abstract only).

Wang TN, et al., The effect of thrombospondin on oral squamous carcinoma cell invasion of collagen. Am J surg. 1995; 170:502-505. (Abstract only).

Clezardin P, et al., Expression of thrombospondin (TSP1) and its receptors (CD36 and CD51) in normal, hyperplastic, and neoplastic human breast. Cancer Res. 1993; 53: 1421-1430. (Abstract only).

Frieda S, et al., Recombinant GST/CD36 fusion proteins define a thrombospondin binding domain. Evidence for a single calcium-dependent binding site on CD 36. J Biol Chem. 1995; 270:2981-2986. (Abstract only).

Arnoletti JP et al., Computer-assisted analysis of tumor sections for a new thrombospondin receptor. Am J Surg.1994; 168:433-436. (Abstract only).

Begany A, et al., Expresson of thrombospondin-1 (TSP1) and its receptor (CD36) in healthy and diseased human skin. Acta Derm Vemereol.1994; 74: 269-272. (Abstract only).

Tuszynski GP and Nicosia, RF, Localization of thrombospondin and its cysteine-serine-valine-threonine-cysteine-glycine-specific receptor in human breast carcinoma. Lab Invest. 1994; 70:228-233. (Abstract only).

Walz DA. et al., Thrombospondin as a mediator of cancer cell adhesion in metastasis. Cancer Metastasis Rev. 1992; 11: 313-324. (Abstract only).

Baenziger NL et al. Isolation and properties of a thrombin-sensitive protein of human platelets. J. Biol. Chem., 1972. 247:2723-2731.

Bayraktar M. et al. Platelet Factor 4, beta-thromboglobulin and thrombospondin levels in type I diabetes melitus patients. J. Int. Med. Res., 1994, Mar.-Apr.; 22(2):90-94. (Abstract only).

Nathan FE et al: Plasma thrombospondin levels in patients with gynecological malignancies. Cancer, 1994. Jun. 1; 73(11):2853-2858. (Abstract only).

Shen D et al. Effects of hypoxia on platelet activation in pilots. Aviat Space Environ. Med., 1994. Jul.; 65(7):646-648. (Abstract only).

Schultz-Cherry S et al. The type 1 repeats of thrombospondin 1 activate latent transforming growth factor-beta. J. Biol. Chem., 1994. 269(43):26783-26788.

Qian X et al. Expression of thrombospondin-1 in cancer: a role in tumor progression. Proc. Soc. Exp. Biol. Med., 1996. Jul.; 212(3):199-207.

Levine DM and William KJ. Automated measurement of mouse apolipoprotein B: convenient screening tool for mouse models of atherosclerosis. Clin. Chem., 1997. 43(4):669-674. (Abstract only).

Partin AW et al. Combination of prostate-specific antigen, clinical stage, and Gleason score to predict pathological stage of localized prostate cancer. A multi-institutional update. JAMA, 1997. 277(18):1445-1451. (Abstract only).

Yamashita Y et al. Plasma thrombospondin levels in patients with colorectal carcinoma. Cancer, 1998. Feb 15; 82(4):632-638. (Abstract only).

Goundis D et al. Properdin, the terminal complement components, thrombospondin and the circumsporozite protein of malaria parasites contain similar sequence motifs. Nature, 1988. Sep. 1; 335(6185):82-5. (Abstract only).

Ozatli D et al. Circulating thrombomodulin, thrombospondin, and fibronectin in acute myeloblastic leukemias. Haematologia (Budap.), 1999. 29(4):277-283. (Abstract only).

Shafiee A et al., Inhibition of Retinal Angiogenesis by Peptides Derived from Thrombospondin-1. Invest Opthamol Vis Sci. 2000; 41: 2378-2388.

Hugo CPM et al, Thrombospondin peptides are potent inhibitors of mesangial and glomerular endothelial cell proliferation in vitro and in vivo. Kidney International. 1999; 55: 2236-2249.

Taraboletti G et al.; The heparin binding 25 kDa fragment of thrombospondin-1 promotes angiogenesis and modulates gelatinase and TIMP-2 production in endothelial cells. The Faseb Journal. 2000; 14:1674-1676.

Damas C et al., The 33-kDa Platelet α-granule Membrane Protein (GMP-33) is an N-terminal Proteolytic Fragment of Thromobospondin. Thrombosis and Haemostasis. 2001; 86: 887-893.

Kuroi K et al.; Circulating angiogenesis regulators in cancer patients. Int J Biol Markers. 2001; 16: 5-26.

Morandi V et al.; Characterization of a novel monoclonal antibody (V58A4) raised against a recombinant NH2-terminal heparin-binding fragment of human endothelial cell thrombospondin. FEBS Letters. 1994; 346: 156-160.

* cited by examiner

Figure 1: Thrombospondin and fragments

THROMBOSPONDIN FRAGMENTS AND BINDING AGENTS IN THE DETECTION, DIAGNOSIS AND EVALUATION OF CANCER

CROSS REFERENCE TO RELATED APPLICATIONS

This application claims the benefit of U.S. provisional application 60/405,494 filed Aug. 23, 2002.

FIELD OF THE INVENTION

The present invention relates to assays for blood levels of one or more thrombospondin fragments as a diagnostic test for cancers and other diseases, the use of such fragments and/or derivatives thereof to generate specific antibodies and other binding agents and/or to use as calibrators, competitors, and/or indicators in an assay, and to the fragments themselves.

BACKGROUND OF THE INVENTION

Thrombospondin (TSP), also known as TSP-1, is a multimeric glycoprotein comprised of identical monomers. The monomers migrate at an apparent molecular weight of approximately 185 kDa in SDS-polyacrylamide electrophoretic gels under reducing conditions. The predominant multimer is a trimer, which migrates at an apparent molecular weight of approximately 450 kDa on non-reducing gels. The molecular weights by sedimentation equilibrium are similar, at 135 kDa for monomers and 420 kDa for trimers. The predicted molecular weight from just the sequence of amino acyl residues in the monomer is 127,524 Da, which does not include contributions from glycosylation and $\beta$-hydroxylation. The thrombospondin glycoprotein is produced by platelets and is released upon platelet activation from platelet $\alpha$-granules, along with many other proteins, such as platelet-derived growth factor, $\beta$-thromboglobulin, fibronectin, fibrinogen, and platelet factor-4 (see Chapter 1, "An introduction to the thrombospondins" in *The Thrombospondin Gene Family* by J C Adams, R P Tucker, & J Lawler, Springer-Verlag: New York, 1995, pp. 1-9, but especially p. 2; and Chapter 3, "The secondary and tertiary structure of the thrombospondins," *ibidem* pp. 43-56, especially Table 3.1). Thrombospondin is known to be involved in biological processes such as cell adhesion, proliferation and chemotaxis. It has also been reported that thrombospondin may be involved in the progression of malignant tumors. Furthermore, thrombospondin has been reported to be highly expressed in many human malignant tissues and in surrounding stroma and/or endothelium and has been reported to be present in higher than normal levels in the plasma of cancer patients. (e.g., Qian and Tuszynski, *Proc. Soc. Exp. Biol. Med.,* 212:199-207, 1996; de Fraipont F et al. *Trends Mol. Med.,* 7:401-407, 2001).

Despite the foregoing, as for any potential diagnostic test, it would be desirable to increase the specificity and sensitivity of such tests. To that end, the present inventor has discovered that thrombospondin is present in the blood in relatively small amounts compared to fragments of thrombospondin, and this finding is true in the plasma of cancer patients as well. This discovery provided a basis for the present inventions related to novel diagnostic assays that are more specific, more sensitive, more easily calibrated, and in some cases distinguish these thrombospondin fragments from each other and from thrombospondin itself.

BRIEF SUMMARY OF THE INVENTION

Important aspects of the invention are diagnostic methods and related kits that are based on the detection and quantification of thrombospondin fragments and/or thrombospondin in bodily fluids, especially plasma. Foremost among those diagnostic methods are those that detect or monitor the status of cancer.

Aspects of the invention closely related to the diagnostic methods are thrombospondin fragments that are detected in the plasma, thrombospondin fragments that can be used to induce antibodies of interest for use in the diagnostic methods or can be used in competition-type or non-competitive diagnostic assays.

Thrombospondin Fragments of the Invention

In one aspect, the invention is a purified thrombospondin fragment that has been extracted from a bodily fluid, especially plasma, said fragment being one within a molecular weight range selected from the group consisting of 80 to 110 kDa, 40 to 60 kDa, and 20 to 35 kDa, wherein the size in kDa is that determined by gel electrophoresis after disulfide bond reduction. Their uses include the induction of antibodies of interest in the diagnostic methods, use in competition-type diagnostic assays, and as reference molecules in assays for thrombospondin fragments of human subjects. In a closely related aspect, the invention is a polypeptide or modified polypeptide, made by recombinant and/or chemical techniques, that has the identical primary structure as one of said purified thrombospondin fragments.

In particular embodiments, the fragment's molecular weight is one within a molecular weight range selected from the group consisting of 85 to 95 kDa, 47 to 53 kDa, and 27 to 33 kDa. Specific examples of fragment molecule weights are 85, 90, 50, and 30 kDa. Preferably, the fragment is one found in human plasma.

In a related aspect, the invention is a purified and/or synthetic thrombospondin fragment or portion thereof, said fragment being one that starts between amino acid I-165 (just after the N12/I peptide) and V-263 (the start of the procollagen homology domain), inclusive (i.e., inclusive of I-165 and V-263), and ends between amino acid K-412 (the end of the reported collagen type V-binding region) and I-530 (the end of the domain of type 1 repeats), inclusive. Preferred are such fragments that start at between N-230 and G-253, inclusive (at or near the start of the domain of interchain disulfide bonds, I-241, which is the first residue downstream [meaning towards the C-terminus of the full protein] of a predicted cleavage site for chymotrypsin and/or a chymotrypsin-like protease), and end at between V-400 and S-428, inclusive (at or near a predicted chymotrypsin cleavage site, F-414, that falls two residues after the end of the collagen type V-binding region), said portion being at least 3 amino acyl acids in length (preferably at least 4 amino acyl residues in length, more preferably at least 6 amino acyl residues).

In a further related aspect, the invention is a purified and/or synthetic thrombospondin fragment or portion thereof, said fragment being one that starts between amino acid I-165 (just after the N12/I peptide) and V-263 (the start of the procollagen homology domain), inclusive, and ends between amino acid I-530 (the end of the type 1 repeats) and R-733 (the end of the first type 3 repeat), inclusive. Preferably such a fragment starts between N-230 and G-253, inclusive, and ends between D-527 and S-551, inclusive, which is at or near a predicted chymotrypsin cleavage site, F-539, in the first type 2 repeat; said portion being at least 3 amino acyl acids in length (preferably at least 4 amino acyl residues in length, more preferably at least 6 amino acyl residues).

In a still further related aspect, the invention is a purified and/or synthetic thrombospondin fragment or portion thereof, said fragment being one that starts between amino acid I-165 (just after the N12/I peptide) and V-263 (the start of the procollagen homology domain), inclusive, and ends between amino acid R-792 (the end of the third type 3 repeat) and Y-982 (the third of the predicted chymotrypsin cleavage sites in the C-terminal domain), inclusive. Preferably such a fragment starts between N-230 and G-253, inclusive, and ends between G-787 and V-811, inclusive, which is at or near a predicted chymotrypsin cleavage site, Y-799, in the fourth type 3 repeat; said portion being at least 3 amino acyl acids in length (preferably at least 4 amino acyl residues in length, more preferably at least 6 amino acyl residues). Protein molecular weights here were computed using standard computational aids (such aids are available, for example, at the web site of the Bioinformatics Organization, Inc; see Stothard, P. 2000. The sequence manipulation suite: JavaScript programs for analyzing and formatting protein and DNA sequences. Bio Techniques 28: 1102-1104) and adjusted upwards to account for post-translational modifications. Predicted cleavage sites for chymotrypsin (and any closely related protease) were identified using tools available from the ExPASy (Expert Protein Analysis System) proteomics server of the Swiss Institute of Bioinformatics (SIB) and were limited to predicted sites of at least 80% probability. The uses of said fragments and portions include, but are not limited to, the induction and/or screening of antibodies and other binding agents of interest in the diagnostic methods and use in diagnostic assays. In particular embodiments, the invention is one of the specified fragments, rather than a portion thereof. In additional embodiments, a fragment and/or a portion can incorporate or be linked to a label and/or a carrier.

Throughout, wherever reference is made to a fragment or a portion thereof (or an immunoreactive portion thereof), it is understood that the fragment is a preferred embodiment of the invention. It is also understood throughout this Application that immunogenic portions, immunoreactive portions, and/or epitopes are generally six amino acyl residues long or longer, but an occasional portion or epitope can be shorter. Such shorter portions or epitopes are also contemplated.

Five additional aspects are:

1) A purified and/or synthetic thrombospondin fragment, said fragment being at least 6 contiguous amino acyl residues in length, and wherein the fragment comprises a protease-resistant core domain or a part thereof, said domain or part thereof being selected from the group consisting of a domain of inter-chain disulfide bonds, an oligomerization domain, a procollagen-like domain, a type 1 repeat, a type 2 repeat, and a type 3 repeat, said part being at least 6 amino acyl residues in length.

2) A purified and/or synthetic thrombospondin fragment, said fragment being at least 6 contiguous amino acyl residues in length, and wherein the fragment comprises an amino acid sequence selected from the group consisting of TEENKE (SEQ ID NO:1), CLQDSIRKVTEENKE (which includes an N-terminal Cys added to aid conjugation) (SEQ ID NO:2), LQDSIRKVTEENKE (SEQ ID NO:3), EGEARE (SEQ ID NO:4), PQMNGKPCEGEARE (SEQ ID NO:5), EDTDLD (SEQ ID NO:6), YAGNGIICGEDTDLD (SEQ ID NO:7), CNSPSPQMNGKPCEGEAR (SEQ ID NO:8), RKVTEENKELANELRRP (SEQ ID NO:9), CRKVTEENKELANELRRP (which includes an N-terminal Cys added to aid conjugation) (SEQ ID NO:10), PQMNGKPCEGEAR (SEQ ID NO:11), CEGEAR (SEQ ID NO:12), and RKVTEENKE (SEQ ID NO:13). (in particular embodiments the fragment comprises two, or even all of the foregoing sequences).

3) a purified and/or synthetic thrombospondin fragment, said fragment being at least 6 contiguous amino acyl residues in length, and wherein the fragment comprises a collagen type V binding domain or a portion thereof.

4) A purified and/or synthetic thrombospondin fragment, said fragment being at least 6 contiguous amino acyl residues in length, and wherein the fragment comprises an epitope for binding the commercially available TSP Ab-4 antibody (also known as mAb A6.1, from clone A6.1, Lab Vision Corporation, Fremont, Calif., see published literature about this clone, such as Galvin NJ et al. Interaction of human thrombospondin with types I-V collagen: direct binding and electron microscopy. *J Cell Biol.* 1987 May;104(5):1413-22).

5) A purified and/or synthetic thrombospondin fragment, said fragment being at least 6 contiguous amino acyl residues in length, and wherein the fragment does not comprise at least one fibrinogen-binding region selected from the group consisting of (1) a fibrinogen-binding domain within a 210-kDa fragment of TSP, where said 210-kDa fragment is composed of three 70-kDa fragments that contain the region of inter-chain disulfide bonds, the procollagen homology region, and the type 1 and type 2 repeats, (2) a fibrinogen-binding region in the amino-terminal domain of thrombospondin, (3) a fibrinogen-binding region in an 18-kDa amino-terminal heparin-binding domain of thrombospondin, and (4) a region corresponding to synthetic peptide N12/I encompassing amino acid residues 151-164 (I-151 to P-164) of the N-terminal domain of thrombospondin-1. In a particular embodiment, the fragment does not comprise any of the fibrinogen-binding regions in the group.

For each of the 5 additional aspects, the molecular weight of the thrombospondin fragment does not exceed 110 kDa; alternatively does not exceed 55 kDa; or alternatively does not exceed 35 kDa, wherein the size in kDa is that determined by gel electrophoresis after disulfide bond reduction. The fragments of the 5 additional aspects of the invention can be used to induce antibodies (and/or other binding molecules) of interest in the diagnostic methods or can be used in diagnostic assays, for example, as calibrators, indicators, and/or competitors. It is understood that a fragment can be derivatized, for example, to incorporate and/or be coupled to a label and/or a carrier.

A fragment that can be as little as 6 amino acyl residues in length is preferably immunoreactive. A typical method for immunizations comprises coupling the peptide to a carrier, such as keyhole limpet hemocyanin or ovalbumin. Said couplings to a carrier are also contemplated in the current invention.

The inclusion of the central protease-resistant core domain in the definition of the fragments follows from considerations discussed elsewhere herein. This domain is considered to comprise locations in the mature thrombospondin protein selected from the group consisting of: a domain of interchain disulfide bonds (around Cys-252 and Cys-256, preferably residues 241-262); the procollagen homology domain (residues 263-360); the type 1 repeats (residues 361-530); the type 2 repeats (residues 531-673); there is a short segment (residues 674-697) between the type 2 repeat domain and the type 3 repeat domain; and then the type 3 repeats (residues 698-925); see FIG. 1 of this Application for examples of protease-resistant fragments that have been reported after artificial digestions in vitro; Chapter 2, "The primary structure of the thrombospondins" in in *The Thrombospondin Gene Family* by J C Adams, R P Tucker, & J Lawler, Springer-Verlag: New York, 1995, pp. 11-42, particularly p. 12; and Chapter 6, "Mechanistic and functional aspects of the interactions of thrombospondins with cell surfaces," ibidem, pp. 105-157, particularly p. 115. Interchain disulfide bonds (in the region of residues 241-262) are often preserved in protease-resistant fragments. The term "mature", as used here to refer to the mature thrombospondin protein sequence, means without the 18- to 22-residue signal peptide sequence, here assumed to be 18 residues, following The Thrombospondin Gene Family by J C Adams el al. 1995; see the full human thrombospondin sequence given below in this text; see also FIG. 1 of this application, and the discussions thereof. Nevertheless, it is understood that GenBank file NM_003246.1, also listed as GI:4507484, currently identifies nucleotide residues "112 . . . 204" as encoding the signal peptide, which implies a signal peptide of 31 amino acyl residues).

The identification of these peptides, TEENKE (SEQ ID NO:1), LQDSIRKVTEENKE (SEQ ID NO:3), EGEARE (SEQ ID NO:4), PQMNGKPCEGEARE (SEQ ID NO:5), EDTDLD (SEQ ID NO:6), YAGNGIICGEDTDLD (SEQ ID NO:7), CNSPSPQMNGKPCEGEAR (SEQ ID NO:8), RKV-TEENKELANELRRP (SEQ ID NO:9), PQMNGK-PCEGEAR (SEQ ID NO:11), CEGEAR (SEQ ID NO:12), and RKVTEENKE (SEQ ID NO:13)was achieved by computerized surveys of thrombospondin, the surveys done by request at commercial sources to identify immunogenic regions (epitopes), but these surveys identified many peptides with immunogenic regions, and so the surveys were followed by selection of relevant peptides and/or epitopes based on knowledge of circulating thrombospondin fragments. Other peptides and/or epitopes listed in this application were similarly identified.

A criterion that a fragment comprise an immunogenic and/or immunoreactive portion from a collagen type V binding domain follows from the published properties (e.g., Galvin N J et al. Interaction of human thrombospondin with types I-V collagen: direct binding and electron microscopy. J. Cell Biol. 1987 May;104(5):1413-22) of the commercially available TSP Ab-4 antibody used below to detect thrombospondin fragments of interest in the plasma.

The collagen V-binding domain of thrombospondin has been mapped to the amino acid sequence corresponding to the region between valine(333) and lysine(412) (V-333 to K-412, using the single-letter symbols V and K for their respective amino acids), inclusive, of human thrombospondin-1 (Takagi T et al. A single chain 19-kDa fragment from bovine thrombospondin binds to type V collagen and heparin. J Biol Chem 268:15544-15549, 1993; as mentioned above, numbers here refer to the mature thrombospondin protein, that is, without the 18- to 22-residue signal peptide sequence, here assumed to be 18 residues). This region would include a portion of the procollagen homology region of thrombospondin and all or nearly all of the first type 1 repeat of thrombospondin (see Chapter 2, "The primary structure of the thrombospondins" in The Thrombospondin Gene Family by J C Adams, R P Tucker, & J Lawler, Springer-Verlag: New York, 1995, pp. 11-42, but especially p. 24).

The criterion that the fragment comprise an epitope for binding the commercially available TSP Ab-4 antibody follows from the fact that the TSP Ab-4 antibody was used below to successfully detect thrombospondin fragments of interest in the plasma, including the plasma of cancer patients. Significantly, this TSP Ab-4 antibody is described as binding the collagen type V binding domain of thrombospondin.

For references regarding a fibrinogen-binding region within a 210-kDa fragment of TSP composed of three 70-kDa fragments that contain the region of interchain disulfide bonds, the procollagen homology region, and the type 1 and type 2 repeats, see p.24 of Adams el al. The Thrombospondin Gene Family; citation 53 therein, which is Lawler J et al. Thrombin and chymotrypsin interactions with thrombospondin. Ann N Y Acad Sci. 1986;485:273-87; and citations immediately below. Additional references for the fibrinogen-binding regions to be excluded include: for a region in an 18-kDa amino-terminal heparin-binding domain of thrombospondin (so-called TSP 18), see Bonnefoy A et al.: A model of platelet aggregation involving multiple interactions of thrombospondin-1, fibrinogen, and GPIbIITTa receptor. J Biol Chem. 2001 Feb 23;276(8):5605-12. For a region corresponding to synthetic peptide N12/I encompassing amino acid residues 151-164 of the N-terminal domain of thrombospondin-1, see Voland C et al.: Platelet-osteosarcoma cell interaction is mediated through a specific fibrinogen-binding sequence located within the N-terminal domain of thrombospondin 1. J Bone Miner Res. 2000 Feb; 15(2):361-368. Citations for two fibrinogen-binding domains include p. 24 of Adams et al. The Thrombospondin Gene Family (and citations 51-54 therein), and for the role of the type 1 repeats include Panetti T S et al.: Interaction of recombinant procollagen and properdin modules of thrombospondin-1 with heparin and fibrinogen/fibrin. J Biol Chem. 1999 Jan 1;274(1):430-7.

Thrombospondin is a glycosylated protein. Therefore, depending on which portion of thrombospondin is considered, the thrombospondin fragments of the invention may be glycosylated or non-glycosylated. Potential sites for N-linked carbohydrate chains include N-230 (in the N-terminal domain), N-342 (in the procollagen homology domain), N-503 (in the type 1 repeat domain), N-690 (in the region between the type 2 and type 3 repeat domains), N-1033 (in the C-terminal domain), and N-1049 (in the C-terminal domain). It is also understood that specific C- and O-linked saccharide attachments occur, particularly in the type 1 repeat domain (see Hofsteenge J, Huwiler K G, Macek B, Hess D, Lawler J, Mosher D F, Peter-Katalinic J: C-mannosylation and O-fucosylation of the thrombospondin type 1 module. J Biol Chem. 2001 Mar 2;276(9):6485-6498). It is also understood that β-hydroxylation of thrombospondin can occur (such as at N-592, which is in the type 2 repeat domain; see FIG. 2.2a in Adams J C et al. The Thrombospondin Gene Family, 1995, p. 16), and that any of these modifications can be incorporated, or not, into thrombospondin fragments and/or peptides of the current invention.

Nonglycosylated entities of particular interest are synthetic peptides.

In particular embodiments, the thrombospondin fragments of the invention are derivatized so that they comprise and/or are linked to a detectable label and/or a carrier. In particular embodiments, the label is selected from the group consisting of a radioactive label, a fluorescent label, a chemical label, a colorometric label, an enzymatic label, a non-fluorescent label, a non-radioactive label, a biotin moiety, and an avidin moiety. In particular embodiments, the carrier is selected from the group consisting of a bead, a microsphere, a coded microsphere, a solid matrix, a keyhole limpet hemocyanin, an albumin, linkage to a cross-linking agent, an epitope tag, and an epitope.

It is understood that a synthetic or purified thrombospondin fragment of the invention retains its identity as a fragment of the invention even if it has been derivatized by the addition of additional material, such as detectable label, or through conjugation to another molecule, or by synthesizing it as part of a chimeric protein, to name just three of many possible examples.

Binding Agents

The detection of either thrombospondin fragments or thrombospondin usually requires the use of agents that will bind to them. Such agents may be multi-chain antibodies, single-chain antibodies, proteins that are not antibodies, non-protein molecules, or derivatives or combinations thereof. Polyclonal and monoclonal antibodies are normally immunoglobulins, i.e., multi-chain antibodies. In the case of immunoglobulin-G (IgG), each antibody molecule consists of a pair of heavy chains and a pair of light chains. The multichain antibodies are typically from mammalian or avian sources. Single-chain antibodies and non-antibodies are discussed below.

The term "antibodies" by itself, when not specified as being a single-chain antibodies, refers to 4-chain antibodies, those with two heavy and two light polypeptide chains. By way of example, this includes but is not limited to the IgG classes of antibodies, but also other classes, such as ones that occur in higher multimers, such as IgM. IgA and IgY are also contemplated.

The term "protein" is intended to include not only molecules normally referred to as proteins but also those that may be referred to as polypeptides.

Methods of Detecting the Thrombospondin Fragments while Distinguishing, or Not Distinguishing, from Thrombospondin Itself In one such an aspect, the invention includes an assay to detect a thrombospondin fragment of the invention wherein the assay distinguishes the thrombospondin fragment from thrombospondin itself. The thrombospondin fragments of particular interest are ones found in humans and are within a range selected from the group consisting of 80 to 100 kDa, 40 to 55 kDa and 20 to 30 kDa, wherein the size in kDa is that determined by gel electrophoresis after disulfide bond reduction Most preferably they are selected from the group consisting of an ~85 kDa to 90 kDa fragment, an ~50 kDa fragment, and an ~30 kDa fragment. The assay may detect just one such fragment, or a combination of 2 or more.

In cases where the concentration of higher molecular weight forms, including thrombospondin itself, is low in a sample (such as in the samples shown in FIGS. 3 and 4, Results of Western Blot analysis using TSP Ab-4 antibody), detection of fragments without necessarily excluding thrombospondin is an approach also contemplated by the current invention. Low concentrations of thrombospondin can be achieved in many cases by preventing or reducing platelet activation during sample collection and/or storage (see below for contemplated methods). This aspect of the current invention comprises several advantages over conventional detection methods that have used binding agents against the entire thrombospondin molecule (and these binding agents have been limited to antibodies). Said advantages include but are not limited to the use of binding agents that are directed specifically against the fragments of interest and not portions of the thrombospondin molecule outside of these fragments, the use of relevant peptides and/or thrombospondin fragments to generate said binding agents (such as antibodies), the use of relevant peptides and/or thrombospondin fragments as assay calibrators, and the use of relevant peptides and/or thrombospondin fragments as assay indicators.

Any of several acceptable approaches can be used for the assay of a thrombospondin fragment (or fragments) wherein the assay distinguishes it from thrombospondin, and more than one of these can be used in a given assay. In one approach, the assay comprises a step wherein the fragment is physically separated from the thrombospondin. Generally that approach is combined with a step in which the presence of the fragment or thrombospondin is shown by their reaction with a specific binding agent. In particular embodiments, the physical separation technique is selected from the group consisting of gel electrophoresis, dialysis, chromatography, size chromatography, affinity chromatography, immunoaffinity chromatography, adsorption, immunoadsorption, isoelectric focusing, mass spectrometry, centrifugation, sedimentation, floatation, precipitation, immunoprecipitation, and gel filtration.

In a second approach, the assay distinguishes the fragment (or fragments) based on one or more epitopes (here "epitope" meaning a target to which a binding agent, i.e., an antibody or a non-antibody, binds) in the fragment that are not present in thrombospondin, including but not limited to an epitope at an end of a fragment and an epitope that is displayed by a fragment but is shielded in thrombospondin.

In a third approach, the assay distinguishes the fragment (or fragments) based on one or more epitopes in thrombospondin that are not present in the fragment. As an illustrative but not restrictive example, an epitope shared by thrombospondin and a thrombospondin fragment is used to obtain a quantitation of a total, thrombospondin plus thrombospondin fragment (s), from which is then subtracted a quantitation of thrombospondin obtained using an epitope present in thrombospondin but not present in a fragment. The difference between the two quantitations is a quantitation of the amount of fragment. As an example, epitopes in thrombospondin but not in at least one fragment from the group of an 80 to 100 kDa, a 40 to 55 kDa, or a 20 to 35 kDa fragment present in plasma can be selected from the group consisting of an epitope from outside the protease-resistant central core domain, an epitope in the N-terminal domain, an epitope in the N-terminal heparin-binding domain, a heparin- binding sequence in the N-terminal domain, a heparin-binding sequence in the N-terminal domain selected from the group consisting of residues 23-32 (RKGSGRRLVK SEQ ID NO: 59), residues 23-29 (RKGSGRR SEQ ID NO: 60), and residues 77-83 (RQMKKTR SEQ ID NO: 61) of the mature protein (see Chapter 2, "The primary structure of the thrombospondins" in The Thrombospondin Gene Family by J C Adams, R P Tucker, & J Lawler, Springer-Verlag: New York, 1995, pp. 11-42, but especially p. 13 & Table 2.1; Chapter 6, "Mechanistic and functional aspects of the interactions of thrombospondins with cell surfaces," ibidem pp. 105-157, but especially pp. 108 & 114; Lawler J et al. Expression and mutagenesis of thrombospondin. Biochemistry. 1992 Feb 4; 31 (4): 1173-80; and Cardin A D & Weintraub H J. Molecular modeling of protein-glycosaminoglycan interactions. Arteriosclerosis. 1989 Jan-Feb ; 9 (1) : 21-32), a heparin-binding sequence in the N-terminal domain selected from the group consisting of residues 22-29 (ARKGSGRR (SEQ ID NO: 62)), residues 79-84 (MKKTRG (SEQ ID NO: 63)), and residues 178-189 (RLRIAKGGVNDN (SEQ ID NO: 64)) of the mature protein (reviewed in the Discussion section of Voland C et al.: Platelet-osteosarcoma cell interaction is mediated through a specific fibrinogen- binding sequence located within the N-terminal domain of thrombospondin 1. J Bone Miner Res. 2000 Feb; 15 (2): 361-368). an epitope in the C-terminal domain, an epitope in the C-terminal cell-binding domain, a thrombospondin epitope not found in a plasma fragment, a thrombospondin epitope not found in a plasma fragment of 80 to 100 kDa, a thrombospondin epitope not found in a plasma fragment of 40 to 55 kDa, and a thrombospondin epitope not found in a plasma fragment of 20 to 35 kDa, where all kDa molecular weights are those after reduction. It is understood that the absence of a strong, functional heparin-binding domain from a thrombospondin fragment in plasma will be a factor allowing its accumulation in plasma (many heparin-or heparan-binding proteins are cleared from plasma very quickly ; see for example, Wallinder L et al. Rapid removal to the liver of intravenously injected lipoprotein lipase. Biochim Biophys Acta. 1979 Oct 26; 575 (1): 166-73).

The epitopes may be divided into three Groups. Group 1: An epitope shared by thrombospondin and a thrombospondin fragment present in plasma is preferably one that is contained within an amino acid sequence selected from the group consisting of TEENKE (SEQ ID NO:1), CLQDSIRKVTEENKE (which includes an N-terminal Cys added to aid conjugation) (SEQ ID NO:2), LQDSIRKVTEENKE (SEQ ID NO:3), EGEARE (SEQ ID NO:4), PQMNGKPCEGEARE (SEQ ID NO:5), EDTDLD (SEQ ID NO:6), YAGNGIICGEDTDLD (SEQ ID NO:7), CNSPSPQMNGKPCEGEAR (SEQ ID NO:8), RKVTEENKELANELRRP (SEQ ID NO:9), CRKVTEENKELANELRRP (SEQ ID NO:10), PQMNGKPCEGEAR (SEQ ID NO:11), CEGEAR (SEQ ID NO:12), RKVTEENKE (SEQ ID NO:13), or a portion at least 3 amino acyl residues in length (preferably at least 4 amino acyl residues in length, more preferably at least 6 amino acyl residues) of such an amino acid sequence.

Group 2: An epitope in thrombospondin but not in an 80 to 100 kDa, 40 to 55 kDa, and/or 20 to 35 kDa fragment present in plasma is preferably one contained within an amino acid sequence selected from the group consisting of TERDDD (SEQ ID NO: 24), DFSGTFFINTERDDD (SEQ ID NO: 25), ERKDHS (SEQ ID NO: 26), TRGTLLALERKDHS (SEQ ID NO: 27), CTRGTLLALERKDHS (SEQ ID NO: 28) (which includes an N-terminal Cys added to aid conjugation), DDKFQD (SEQ ID NO: 29), ANLIPPVPDDKFQD (SEQ ID NO: 30), CANLIPPVPDDKFQD (SEQ ID NO: 31) (which includes an N-terminal Cys added to aid conjugation), DCEKME (SEQ ID NO: 32), EDRAQLYIDCEKMEN (SEQ ID NO: 33) (although it is understood that this sequence and its fragments impinge on the sequence of the fibrinogen-binding N12/I peptide), CGTNRIPESGGDNSVFD (SEQ ID NO: 34), NRIPESGGDNSVFD (SEQ ID NO: 35), GWKDFTAYRWRLSHRPKTG (SEQ ID NO: 36), CGWKDFTAYRWRLSHRPKTG (SEQ ID NO: 37) (which includes an N-terminal Cys added to aid conjugation), or a portion at least 3 amino acyl residues in length (preferably at least 4 amino acyl residues in length, more preferably at least 6 amino acyl residues) of such an amino acid sequence.

Various modifications, such as a C-terminal Cys, can be added to a peptide of interest to allow easier conjugation to a carrier protein such as KLH, ovalbumin, and others. This is particularly true for the following peptides: RKVTEENKELANELRRP (SEQ ID NO: 9), LQDSIRKVTEENKE (SEQ ID NO: 3); TRGTLLALERKDHS (SEQ ID NO: 27), and ANLIPPVPDDKFQD (SEQ ID NO: 30), and these modifications provide alternative conjugation strategies for NRIPESGGDNSVFD (SEQ ID NO: 35) and others.

In approaches related to the above, the assay can distinguish fragments from each other, based on physical separation methods and/or on shared and/or non-shared binding agent targets. Thus, for example, size-exclusion chromatography and/or SDS-polyacrylamide gel electrophoresis can be used to separate the ~85 to 90, ~50-, and ~30-kDa fragments from each other, for separate quantitation (an example of this is shown in FIG. 3, with the quantitation presented in Table 2). Also, for example, an epitope (meaning a binding agent target) in the ~85 to 90-kDa fragment that is not contained in the ~50- and/or the ~30-kDa fragments can be used to assay it separately, and/or can be used to subtract its contribution from a total to obtain results reflective of the smaller fragments.

Group 3: An additional epitope, useful as a binding agent target for distinguishing a fragment from full-length TSP, and/or distinguishing two fragments of different sizes is preferably one contained within an amino acid sequence selected from the group consisting of DDDDNDKIPDDRDNC (SEQ ID NO: 14), DDDDNDKIPDDRDNC[NH2] (SEQ ID NO: 15), DDDDNDK (SEQ ID NO: 16), NLPNSGQEDYDKDG (SEQ ID NO: 17), CNLPNSGQEDYDKDG (SEQ ID NO: 18), EDYDKD (SEQ ID NO: 19), CPYNHNPDQADTDNNGEGD (SEQ ID NO: 20), CRLVPNPDQKDSDGD (SEQ ID NO: 21), DQKDSDGD (SEQ ID NO: 22), CPYVPNANQADHDKDGKGDA (SEQ ID NO :23), or a portion at least 3 amino acyl residues in length (preferably at least 4 amino acyl residues in length, more preferably at least 6 amino acyl residues) of such an amino acid sequence.

It is also understood that some peptides that contain an epitope shared by thrombospondin and a first thrombospondin fragment present in plasma may contain an epitope that is not shared by a second thrombospondin fragment present in plasma. Said peptides are useful in many applications described herein, including but not limited to distinguishing thrombospondin from said second thrombospondin fragment, distinguishing said first from said second thrombospondin fragment, detecting and/or quantitating thrombospondin, detecting and/or quantitating said first thrombospondin fragment, detecting and/or quantitating said second thrombospondin fragment (in a combination assay described elsewhere herein), and producing a binding agent. Said peptides, which form a subset of Group 1, can be selected from the group consisting of EGEARE (SEQ ID NO: 4), PQMNGKPCEGEARE (SEQ ID NO: 5), EDTDLD (SEQ ID NO: 6), YAGNGIICGEDTDLD (SEQ ID NO: 7), CNSPSPQMNGKPCEGEAR (SEQ ID NO: 8), PQMNGKPCEGEAR (SEQ ID NO: 11), CEGEAR (SEQ ID NO: 12), or a portion at least 3 amino acyl residues in length (preferably at least 4 amino acyl residues in length, more preferably at least 6 amino acyl residues) of such an amino acid sequence.

It is also understood that the current invention also includes antibody and non-antibody molecules that bind these peptides, other peptides of thrombospondin specified herein, fragments thereof, and peptides that contain fragments thereof, as well as assays using a reagent from this list. It is understood that an antibody or a non-antibody that distinguishes thrombospondin from a fragment, or one fragment from another, can be employed to affinity-purify thrombospondin or a fragment.

In embodiments of particular interest, a sample of material (liquid tissue, solid tissue, urine, perspiration, cerebrospinal fluid, a body fluid, blood or a blood component, or stool; most preferably blood plasma) is taken or gathered from an organism (either a human or a non-human, preferably a mammal or a bird in the case of non-humans) and is subject to the assay. The inventions disclosed herein not only apply to fragments of human thrombospondin, but also to fragments of non-human thrombospondin. For example, there is a need to detect the presence of or monitor the status of disease, such as a cancer, in livestock, racehorses, pets, and other economically and/or emotionally important animals. The current inventions meet these needs.

In one set of embodiments, the assay detects the presence of, or monitors the course of, diseases and conditions that can affect plasma levels of thrombospondin fragments. Such diseases include, but are not limited to, many that in the prior art were assumed to affect plasma levels of thrombospondin: a cancer, renal failure, renal disease, atopic dermatitis, vasculitis, acute vasculitis, renal allograft, allergic asthma, diabetes mellitus, myocardial infarction, liver disease, splenectomy, dermatomyositis, polyarteritis nodosa, systemic lupus erythematosus, lupus erythematosus, Kawasaki syndrome, non-specific vasculitis, juvenile rheumatoid arthritis, rheumatoid arthritis, vasculitis syndrome, Henoch-Schonlein purpura, thrombocytopenic purpura, purpura, an inflammatory condition, a condition associated with clotting, a condition associated with platelet activation, a condition associated with intravascular platelet activation, a condition associated with consumption of platelets, heparin-induced thrombocytopenia, disseminated intravascular coagulation, intravascular coagulation, extravascular coagulation, a condition associated with endothelial activation, a condition associated with production and/or release of thrombospondin and/or a thrombospondin fragment, urticaria, hives, angioedema, a drug reaction, an antibiotic reaction, an aspartame reaction, atopic dermatitis, eczema, hypersensitivity, scleroderma, conditions associated with plugging of vessels, a condition associated with a cryofibrinogen, a condition associated with a cryoglobulin, and a condition associated with an anti-cardiolipin antibody.

In embodiments of particular interest, the assay for thrombospondin fragments is done to detect the presence of, or monitor the status of, a cancer in a human and/or in a non-human animal. In additional embodiments of interest, the assay is done to measure the degree of platelet activation.

In measurements of plasma levels of the fragments, it is preferred that the plasma is obtained by a method that prevents or reduces platelet activation and/or activation of a component of the clotting cascade during sample collection and/or storage; and/or by a method that prevents or reduces cleavage of thrombospondin into fragments (or fragments into smaller fragments) during sample collection and/or storage. Platelet activation and/or activation of a component of the clotting cascade during sample collection and/or storage can result in the release of thrombospondin, but also activation of proteases (including but not limited to a protease of the clotting cascade) that can cleave thrombospondin and some thrombospondin fragments, thereby complicating the assay. To prevent or reduce platelet activation during sample collection and/or storage, the method may be one that does not comprise the use of a tourniquet. Also to prevent or reduce platelet activation and/or activation of clotting during sample collection and/or storage, the method may, for example, comprise a step selected from the group consisting of: (1) use of a large-bore needle, (2) discarding of the initial portion of the collected blood, (3) use of a coated needle, (4) use of a coated tubing, (5) storage of sample between −1° C. and 5° C., and (6) separation of plasma within 30 minutes of sample collection. Also to prevent or reduce platelet activation and/or protease activity during sample collection and/or storage, the method may comprise the use of an agent the use of an agent selected from the group consisting of a platelet inhibitor, a protease inhibitor, a serine protease inhibitor, an enzyme inhibitor, an inhibitor of an enzyme that is divalent cation dependent, a heparin, a heparin fragment, a heparan, an anticoagulant, a COX inhibitor, an inhibitor of a cell-adhesion molecule, an inhibitor of a surface receptor, a glycoprotein inhibitor, an inhibitor of a glycoprotein IIb/IIIa receptor, a thrombin inhibitor, an inhibitor of degranulation, a chelator, a citrate compound, theophylline, adenosine, and dipyridamole (Diatube H vacutainers containing citrate, theophylline, adenosine, and dipyridamole are commercially available from Becton Dickinson; see Bergseth G et al. A novel enzyme immunoassay for plasma thrombospondin: comparison with beta-thromboglobulin as platelet activation marker in vitro and in vivo. Thromb. Res. 99:41-50, 2000). Devices that minimize platelet activation and/or protease activity in a sample are also contemplated and include, but are not limited to, a collection tube containing a cocktail of platelet and/or clotting inhibitors, a collection tube containing a protease inhibitor, a collection tube containing an inhibitor of a protease that is or is derived from a blood component, and a device that discards or allows the easy discarding of the initial portion of collected blood. These methods can also be applied to samples of other body fluids.

A related aspect of the invention is a combination diagnostic test (especially for cancer) comprising at least two types of diagnostic tests, one of said tests being the assay for a thrombospondin fragment (or fragments) or a portion (or portions) thereof in plasma, the other assay not being based on a thrombospondin fragment or portion. In one set of embodiments, the test not based on a thrombospondin fragment or portion thereof is selected from the group consisting of an imaging test, a radiographic test, a nuclear medicine test, a magnetic resonance imaging test, a blood test, a biopsy, a genetic test, a guaiac test, a test for fecal occult blood, and a test for fecal blood, a cancer test not based on a thrombospondin fragment or portion thereof, a disease test not based on a thrombospondin fragment or portion thereof, and an endoscopy. In particular embodiments of the foregoing methods, a thrombospondin fragment comprises a detectable label (at least during some part of the method).

Detection can, for example, be part of a screening process. Such a screening could include a comparison against a reference value, involve a comparison against a previous value from the same individual; and/or be done repeatedly and/or periodically (e.g., once a year, once every six months, or once every 2, 3, 4, 5 or 10 years.). It is understood that screening can be performed on humans and/or on non-human animals The foregoing methods are assays to detect a thrombospondin fragment of the invention wherein the assay distinguishes, or does not distinguish, a thrombospondin fragment from thrombospondin, or one thrombospondin fragment from another thrombospondin fragment. In any case, such fragments can be referred to as "target" fragments for purposes of the assay. In many instances it is desirable to have the method also comprise a calibration step or procedure, in which known amounts of a thrombospondin fragment (such as a peptide) are subjected to the method. Such "calibration" fragments are optionally detectably labeled. It is possible to perform the assays in which the target and calibration fragments comprise different detectable labels (or where one is detectably labeled and the other is not).

It is understood that interference resulting from fibrinogen binding to an N-terminal domain of thrombospondin is unlikely to affect the detection of thrombospondin fragments related to the protease-resistant core domain (which lack the N-terminal domain). Nevertheless, assays of thrombospondin could be affected (thus, avoiding that region of the N-terminus when assaying thrombospondin and/or diluting, removing, inhibiting, and/or otherwise compensating for interfering molecules is contemplated).

To compensate for interfering substances in assays for thrombospondin fragments, diluting, removing, inhibiting, and/or otherwise compensating for interfering molecules is contemplated. As an illustrative, but not limiting, example, the inclusion of an inhibitor of thrombospondin-fibrinogen interactions is contemplated. Such an inhibitor is selected from the group consisting of synthetic peptide N12/I encompassing amino acid residues 151-164 of the N-terminal domain of thrombospondin-1 (see Voland C et al.: Platelet-osteosarcoma cell interaction is mediated through a specific fibrinogen-binding sequence located within the N-terminal domain of thrombospondin 1. J Bone Miner Res. 2000 Feb; 15(2):361-8), and an antibody to the cyanogen bromide cleavage fragment composed of residues 241-476 of the carboxyl-terminal end of the alpha chain of fibrinogen (see Tuszynski G P et al.: The interaction of human platelet thrombospondin with fibrinogen. Thrombospondin purification and specificity of interaction. J Biol Chem. 1985 Oct 5;260(22): 12240-5).

Single Chain Antibodies and Non-Antibodies

Raising conventional antibodies (also referred to herein simply as "antibodies" as opposed to "single chain antibodies"; and an example of a conventional antibody is IgG, which is composed of two heavy chains and two light chains) is merely one of a number of methods that are generally based on the approach of random, semi-random, directed, combinatorial, and/or other means for the generation of large numbers of diverse peptides and/or non-peptides, that is then followed by a selection procedure to identify within this large number those peptides and/or non-peptides that bind to a target and/or an epitope within a target. Selection can then be followed by methods for improving the peptides and/or non-peptides to achieve better affinity and/or specificity. These diverse peptides and/or non-peptides may be conventional multi-chain antibodies (polyclonal or monoclonal), single-chain antibodies, or non-antibodies, including but not limited to peptides, products of phage display, aptamers, DNA, RNA, or modified DNA or RNA. Also contemplated are thrombospondin receptors and/or binding proteins (such as a CSVTCG (SEQ ID NO: 54) receptor, a CSVTCG (SEQ ID NO: 54) binding molecule, CD36, angiocidin, 26S proteasome non-ATPase regulatory subunit 4, and/or anti-secretory factor).

A well-known procedure for generation of large numbers of diverse peptides is through phage display, which is then followed by selection and can be further refined through other techniques such as molecular evolution (see, for example, Flores-Flores, C. et al, Development of human antibody fragments directed towards synaptic acetylcholinesterase using a semi-synthetic phage display library. J Neural Transm Suppl. 2002;(62):165-179; Qian, M. D, et al, Anti GPVI-human antibodies neutralizing collagen-induced platelet aggregation isolated from a recombinant phage. Human. Antibodies. 2002;11(3):97-105). scFv constructs can be made by linking variable domains of heavy (VH) and light (VL) chains together via a polypeptide linker (for example, see Asvadi P et al. Expression and functional analysis of recombinant scFv and diabody fragments with specificity for human RhD. J Mol Recognit 15:321-330, 2002). Peptides generated then selected (and then possibly improved) via this approach have been used in ELISAs and ELISA-like assays of their targets (e.g., see Schlattner U et al. Isoenzyme-directed selection and characterization of anti-creatine kinase single chain Fv antibodies from a human phage display library. Biochim Biophys Acta. 2002 Dec 12;1579(2-3):124-32; Oelschlaeger P et al. Fluorophor-linked immunosorbent assay: a time- and cost-saving method for the characterization of antibody fragments using a fusion protein of a single-chain antibody fragment and enhanced green fluorescent protein. Anal Biochem. 2002 Oct 1;309(1):27; Nathan S et al. Phage display of recombinant antibodies toward Burkholderia pseudomallei exotoxin. J Biochem Mol Biol Biophys. 2002 Feb;6(1):45-53; Lu D et al. Fab-scFv fusion protein: an efficient approach to production of bispecific antibody fragments. J Immunol Methods. 2002 Sep 15;267(2):213-26; Zhang W et al. Production and characterization of human monoclonal anti-idiotype antibodies to anti-dsDNA antibodies. Lupus. 2002;11(6):362-9; Reiche N et al. Generation and characterization of human monoclonal scFv antibodies against *Helicobacter pylori* antigens. Infect Immun. 2002 Aug;70(8):4158-64; Rau D et al. Single-chain Fv antibody-alkaline phosphatase fusion proteins produced by one-step cloning as rapid detection tools for ELISA. J Immunoassay Immunochem. 2002;23(2):129-43; and Zhou B et al. Human antibodies against spores of the genus Bacillus: a model study for detection of and protection against anthrax and the bioterrorist threat. Proc Natl Acad Sci U S A. 2002 Apr 16;99(8):5241-6; Baek H et al., An improved helper phage system for efficient isolation of specific antibody molecules in phage display. Nucleic Acids Res. 2002 Mar 1; 30(5):e18).

scFv constructs can be based on antibodies, as in most of the references above, on T-cell receptors (e.g., Epel M et al. A functional recombinant single-chain T cell receptor fragment capable of selectively targeting antigen-presenting cells. Cancer Immunol Immunother. 2002 Dec;51(10):565-573), or on other sequences. Different phage coat proteins have been used to display the diverse peptides (see Gao C et al. A method for the generation of combinatorial antibody libraries using pIX phage display. Proc Natl Acad Sci USA. 2002 Oct 1;99(20):12612-6). For an example of fusion constructs, see Lu D et al. Fab-scFv fusion protein: an efficient approach to production of bispecific antibody fragments. J Immunol Methods. 2002 Sep 15;267(2):213-26.

For an example of molecular evolution to improve binding affinity, see Rau D et al. Cloning, functional expression and kinetic characterization of pesticide-selective Fab fragment variants derived by molecular evolution of variable antibody genes. Anal Bioanal Chem. 2002 Jan;372(2):261-7. Examples of other modifications "to improve affinity or avidity, respectively [include] by mutating crucial residues of complementarity determining regions or by increasing the number of binding sites making dimeric, trimeric or multimeric molecules." (the quote is from a review article, Pini A & Bracci L, Phage display of antibody fragments. Curr Protein Pept Sci. 2000 Sep;1(2):155-169). The initial set of diverse molecules can be enriched by using sequences from animals or humans exposed to or expressing antibodies against the target (see again Zhang W et al. Lupus 2002; and Reiche N et al. Infect Immun 2002).

Single chain antibodies can also be generated by using *Escherichia coli* (see Sinacola J R & Robinson A S, Rapid folding and polishing of single-chain antibodies from *Escherichia coli* inclusion bodies, Protein Expr Purif. 2002 Nov; 26(2):301-308.)

Non-antibodies also include aptamers and non-antibodies that comprise aptamers. Aptamers are DNA or RNA molecules that have been selected (e.g., from random pools) on the basis of their ability to bind to another molecule (discussed for example at the web site of the Ellington lab, in the Institute of Cellular and Molecular Biology, at the University of Texas at Austin, wherein said molecule can be a nucleic acid, a small organic compound, or a protein, peptide, or modified peptide (such as thrombospondin or a portion thereof). An aptamer beacon is an example of a non-antibody that comprises an aptamer (See Hamaguchi N et al., Aptamer beacons for the direct detection of proteins. Anal. Biochem. 2001 Jul 15;294(2):126-131.)

Angiocidin is a CSVTCG-specific tumor cell adhesion receptor, see patent application WO 0105968, also NCBI protein accession number CAC32386.1 and/or CAC32387.1 (corresponding to nucleotide accession numbers AX077201 and AX077202), the amino acid sequences specified by those two protein accession numbers as of the date of filing of this application being incorporated herein by reference. It is understood that anti-secretory factor cDNA contains essentially identical nucleotide sequence (e.g., accession # U24704, 99% match by BLAST alignment) to that of angiocidin, as does the nucleotide sequence for the proteasome (prosome, macropain) 26S subunit, non-ATPase, 4 (PSMD4; e.g., accession # NM_002810, also 99% match by BLAST). Anti-secretory factor has the same amino acid sequence as angiocidin, except that AX077201 has a 9-bp insert compared to AX077202, which would mean an additional three amino acyl residues in the encoded protein. Thus, the terms herein are used interchangeably. The NCBI summary for NM_002810 is as follows: "The 26S proteasome is a multi-catalytic proteinase complex with a highly ordered structure composed of 2 complexes, a 20S core and a 19S regulator. The 20S core is composed of 4 rings of 28 non-identical subunits; 2 rings are composed of 7 alpha subunits and 2 rings are composed of 7 beta subunits. The 19S regulator is composed of a base, which contains 6 ATPase subunits and 2 non-ATPase subunits, and a lid, which contains up to 10 non-ATPase subunits. Proteasomes are distributed throughout eukaryotic cells at a high concentration and cleave peptides in an ATP/ubiquitin-dependent process in a non-lysosomal pathway. An essential function of a modified proteasome, the immunoproteasome, is the processing of class 1 MHC peptides. This gene encodes one of the non-ATPase subunits of the 19S regulator lid. Two alternate transcripts encoding two different isoforins have been described. Pseudogenes have been identified on chromosomes 10 and 21. Transcript Variant: This variant (1) encodes the longer protein (isoform 1)." Other names for the protein from the protein accession file (NP_002801.1) include "proteasome 26S non-ATPase subunit 4 isoform 1; antisecretory factor 1; 26S protease subunit S5a; S5a/antisecretory factor protein; multiubiquitin chain binding protein; 26S proteasome non-ATPase regulatory subunit 4".

Methods of Producing Antibodies against the Fragments of the Invention

In another general aspect, the invention is a method of producing antibodies against an above-noted thrombospondin fragment and/or portion thereof, the method comprising administering such a fragment or portion to an organism (especially a mammal or a bird) capable of producing antibodies. It is understood that said antibodies may comprise monoclonal antibodies and/or polyclonal antibodies. For monoclonal antibodies it is understood that cells from the organism are typically used in the production of hybridomas. For production of antibodies, including monoclonal antibodies, it is understood that any of the thrombospondin fragments and/or portions can be conjugated to a carrier molecule, including but not limited to keyhole limpet hemocyanin and bovine serum albumin, to facilitate the antibody response.

A cell and a cell line for producing the aforementioned monoclonal antibodies are aspects of the invention. Examples of such cells include, but are not limited to, hybridomas, transfected cell lines, and infected cells.

Kits of the Invention

Kits related to the above inventions are themselves aspects of the invention. Such kits are, for example, those that facilitate the determination of the presence of, and/or the amount of, and/or the concentration of, a thrombospondin fragment or fragments in a material taken or gathered from an organism. Such kits optionally comprise a thrombospondin fragment or fragments, or a portion or portions thereof, of the invention. Such kits can comprise a binding agent or agents specific for a thrombospondin fragment, or portion thereof, of interest. They optionally comprise binding agents that will react with thrombospondin but not a fragment or fragments, and/or a portion or portions thereof, of interest. They optionally comprise binding agents that distinguish between thrombospondin and a fragment, and/or between one fragment and another. If intended for solid tissue, the kits may comprise a homogenizing means for extracting a fragment into a solution, which optionally may also be provided. Binding agents of the current invention can also be used for other well-known detection methods, including but not limited to immunohistochemistry.

Preferred binding agents are proteins, although non-proteins are also contemplated. Such proteins include both antibodies and nonantibodies.

Optionally, the kits comprise a means for separating or distinguishing a fragment or fragments (or portions thereof) from thrombospondin. The kits can also include a thrombospondin fragment, a peptide derived from such fragment, or a derivatized fragment or peptide, to facilitate detection and calibration.

In one set of embodiments, the kits are adapted for use in an automated assay, such as one using a clinical autoanalyzer.

Particular kit aspects of the invention can also be summarized as follows:

A kit for the determination of the presence of, and/or the amount of, and/or the concentration of, a thrombospondin fragment or fragments in a material taken or gathered from an organism, said kit comprising a thrombospondin fragment or portion thereof.

A kit for the determination of the presence of, and/or the amount of, and/or the concentration of, one or more thrombospondin fragments in a material taken or gathered from an organism, said kit comprising a binding agent capable of binding said one or more fragments.

Particular embodiments are:

Such kits wherein the binding agent comprises a protein.

Such kits wherein said protein comprises an antibody.

Such kits wherein the antibody is a monoclonal antibody or a polyclonal antibody.

Such kits wherein said protein comprises a fragment of an antibody.

Such kits wherein said protein comprises a single-chain antibody.

Such kits wherein said single chain antibody is derived from a phage display library.

Such kits wherein said protein is a non-antibody, the non-antibody being a protein that is neither a multi-chain antibody nor a single-chain antibody.

Such kits wherein said protein non-antibody is selected from the group consisting of a thrombospondin receptor, a thrombospondin receptor that binds within a protease-resistant core region, a thrombospondin receptor that binds a TSP fragment present in the plasma of a cancer patient, a CSVTCG (SEQ ID NO: 54) receptor, a CSVTCG (SEQ ID NO: 54) binding molecule, a CD36 (which reportedly binds CSVTCG (SEQ ID NO: 54); see Carron J A et al., A CD36-binding peptide from thrombospondin-1 can stimulate resorption by osteoclasts in vitro. Biochem Biophys Res Commun. 2000 Apr 21; 270 (3): 1124-7), angiocidin, anti-secretory factor, 26S proteasome non-ATPase regulatory subunit 4, fragments thereof that bind to their respective targets, and combinations, chimeras, and recombinant versions of said receptors and fragments.

Such kits wherein said binding agent comprises a non-protein.

Such kits wherein said binding agent comprises an aptamer.

Such kits wherein said binding agent comprises angiocidin, anti-secretory factor, and/or 26S proteasome non-ATPase regulatory subunit 4.

Other particular kit aspects of the invention can be summarized as follows:

A kit for the determination of the presence of, and/or the amount of, and/or the concentration of, one or more thrombospondin fragments in a material taken or gathered from an organism, said kit comprising a binding agent that will react with thrombospondin but not with a fragment of interest. Particular embodiments are:

Such kits wherein said binding agent comprises a protein;

Such kits wherein said protein comprises an antibody;

Such kits wherein said antibody is a monoclonal antibody or a polyclonal antibody;

Such kits wherein said protein comprises a fragment of an antibody;

Such kits wherein said protein comprises a single-chain antibody;

Such kits wherein said single chain antibody is derived from a phage display library;

Such kits wherein the protein is a non-antibody, the non-antibody being a protein that is neither an antibody nor a single-chain antibody;

Such kits wherein said non-antibody is selected from the group consisting a an integrin, an RGD receptor, an RFYVVMWK receptor, an RFYVVM receptor, an FYVVMWK receptor, an IRVVM receptor, fragments thereof that bind to their respective targets, and combinations, chimeras, and recombinant versions of said receptors, integrins, and fragments; and Such kits wherein said binding agent comprises an aptamer, meaning a DNA or RNA or related compound, that binds thrombospondin or a thrombospondin fragment.

Such kits wherein said binding agent comprises angiocidin, anti-secretory factor, and/or-26S proteasome non-ATPase regulatory subunit 4.

Several motifs within thrombospondin for binding to many of the receptors referred to above are shown in in FIG. 2.2a of Adams, J. C., et al., The thrombospondin Gene Family, Springer Verlag, New York, 1995, p. 16. A CSVTCG receptor, a CSVTCG binding molecule, an angiocidin, an anti-secretory factor, a CD36, and/or fragments and derivatives thereof will be useful for assaying a thrombospondin fragment in a cancer patient.

Focus on Neoplastic Disease

The invention as it pertains to the detection or monitoring of neoplastic disease can also be summarized as the following:

A method to detect the presence of neoplastic disease in an individual, wherein the method comprises the steps of:

(1) measuring the individual's plasma level of a thrombospondin fragment;

(2) utilizing the result of step (1) in a diagnosis as to whether the individual has a neoplastic disease; said fragment being at least 6 contiguous amino acyl residues in length but less than 110 kDa (preferably less than 100 kDa).

Related is such a method, where the individual referred to therein is a first individual and wherein the method further comprises the steps of:

(3) measuring a second individual's plasma level of the thrombospondin fragment, said second individual considered to not have neoplastic disease;

(4) utilizing the result of step (3) is the diagnosis of whether the first individual has a neoplastic disease. For example, such a method wherein the greater the extent to which the first individual's plasma thrombospondin fragment level exceeds the plasma thrombospondin level of the second individual, the more likely that the diagnosis will be that the first individual has a neoplastic disease and/or a neoplastic disease more advanced than that of the second person. It is also understood that values from the first individual taken over time can be compared with one another, to assess the likelihood of the appearance of disease and/or progression and/or regression of disease. Particular embodiments are:

Such methods wherein the fragment is selected from the group consisting of an ~85 to 90 kDa fragment, and ~50 kDa fragment, and an ~30 kDa fragment, wherein the size in kDa is that determined by gel electrophoresis after disulfide bond reduction;

Such methods wherein the neoplastic disease is selected from the group consisting of an adenoma, adenocarcinoma, carcinoma, lymphoma, leukemia, and sarcoma;

Such methods wherein the neoplastic disease is an internal cancer;

Such methods wherein the neoplastic disease is selected from the group consisting of a cancer of the respiratory system, a cancer of the circulatory system, a cancer of the musculoskeletal system, a cancer of a muscle, a cancer of a bone, a cancer of a joint, a cancer of a tendor or ligament, a cancer of the digestive system, a cancer of the liver or biliary system, a cancer of the pancreas, a cancer of the head, a cancer of the neck, a cancer of the endocrine system, a cancer of the reproductive system, a cancer of the male reproductive system, a cancer of the female reproductive system, a cancer of the genitourinary system, a cancer of a kidney, a cancer of the urinary tract, a skin cancer, a cancer of other sensory organs (such as eye, ear, nose, tongue), a cancer of the nervous system, a cancer of a lymphoid organ, a blood cancer, a cancer of a gland, a cancer of a mammary gland, a cancer of a prostate gland, a cancer of endometrial tissue, a cancer of mesodermal tissue, a cancer of ectodermal tissue, and a teratoma;

Such methods wherein the neoplastic disease is selected from the group consisting of a cancer of solid tissue, a cancer of the blood or the lymphatic system, a non-metastatic cancer, a premetastic cancer, a metastatic cancer, a poorly differentiated cancer, a well-differentiated cancer, and a moderately differentiated cancer.

Such methods wherein the measurement of a plasma thrombospondin fragment level comprises the use of a binding agent, said binding agent being capable of binding said thrombospondin fragment (Such binding agents are discussed above in the context of the kits of the invention); and In particular embodiments, the thrombospondin fragment is separated from thrombospondin before said fragment is bound to the binding agent.

Such methods wherein said method comprises the use of a binding agent, comprising a binding agent capable of binding thrombospondin but not the thrombospondin fragment. Possible binding agents are discussed above in the context of kits of the invention.

In particular embodiments, the thrombospondin fragment is separated from thrombospondin before said fragment is bound to the binding agent.

Related inventions are:

A method of producing antibodies against a thrombospondin fragment, said method comprising administering said fragment to an organism capable of producing antibodies;

Said method of producing antibodies wherein said fragment is at least 6 amino acyl residues in length but less than 110 kDa (preferably less than 95 kDA). A polyclonal antibody preparation produced by said method;

A monoclonal antibody produced by said method;

A cell line producing said monoclonal antibody; and

A method of producing a binding agent against a thrombospondin fragment, said method comprising the use of phage display.

Said method of producing a binding agent, wherein said method comprises the selection of a thrombospondin-binding or thrombospondin fragment-binding phage from a phage display.

Said method of producing a binding agent, wherein said fragment at least 6 amino acyl residues in length.

Cancer Detection Method Comprising Measuring Platelet Activation

An additional general aspect of the invention is an assay for the presence of cancer in an organism, said method comprising measuring the extent of platelet activation.

DETAILED DESCRIPTION OF THE INVENTION

The terms "thrombospondin" and "thrombospondin-1" are used interchangeably herein. It is understood that a single "band" on an electrophoresis gel may in fact reflect the presence of a collection of fragments that together form a population that, during gel electrophoresis under reducing conditions, electrophorese at similar rates.

The terms "test" and "assay" are also used interchangeably.

A "purified" fragment is for example (1) one that is found in human plasma and that has been purified (for example has been isolated from gels on which the plasma has been electrophoresed). A purified fragment is not one that is in human plasma, or other part of a human, and that has not undergone at least some degree of purification.

A "synthesized fragment" is, for example, one that has been synthesized in a laboratory (e.g., by recombinant DNA technology or by chemical synthesis) so as to have the primary structure of such a fragment or a portion thereof.

The amino acid sequence of human thrombospondin-1 from GenBank is:

```
ACCESSION  NM_003246 (protein_id = NP_003237.1)
VERSION    NM_003246.1 GI:4507484
```

(SEQ ID NO: 38)
MGLAWGLGVLFLMHVCGT<u>N</u>RIPESGGDNSVFDIFELTGAARKGSGRRLVK
GPDPSSPAFRIEDANLIPPVPDDKFQDLVDAVRAEKGFLLLASLRQMKKT

Figure 1:
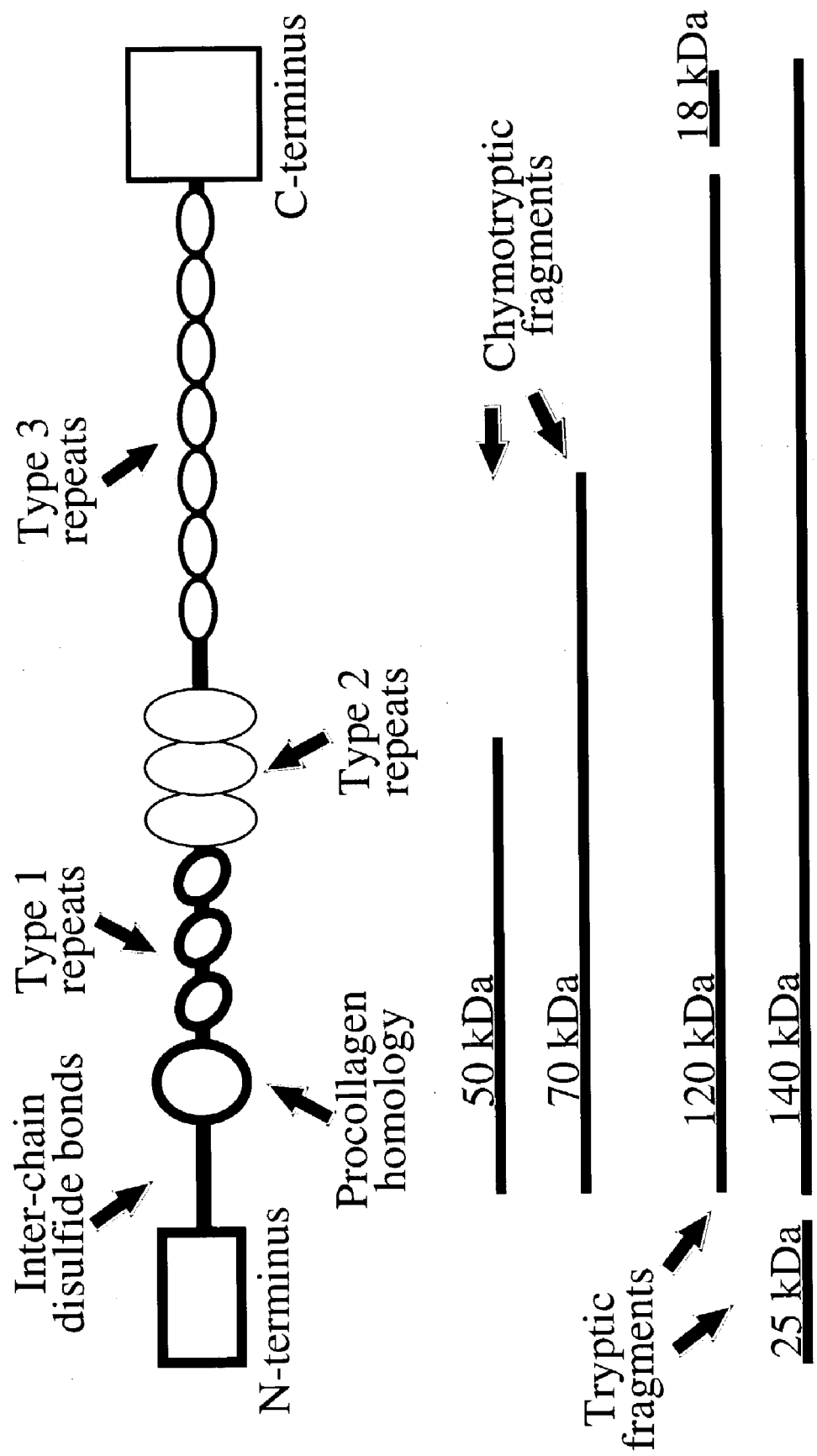
FIG. 1. Schematic drawing of thrombospondin.

-continued
RGTLLALERKDHSGQVFSVVSNGKAGTLDLSLTVQGKQHVVSVEEALLAT
GQWKSITLFVQEDRAQLYIDCEKMENAELDVPIQSVFTRDLASIARLRIA
KGGVNDNFQGVLQNVRFVFGTTPEDILRNKGCSSSTSVLLTLDNNVVNGS
SPAIRTNYIGHKTKDLQAICGISCDELSSMVLELRGLRTIVTTLQDSIRK
VTEENKELANELRRPPLCYHNGVQYRNNEEWTVDSCTECHCQNSVTICKK
VSCPIMPCSNATVPDGECCPRCWPSDSADDGWSPWSEWTSCSTSCGNGIQ
QRGRSCDSLNNRCEGSSVQTRTCHIQECDKRFKQDGGWSHWSPWSSCSVT
CGDGVITRIRLCNSPSPQMNGKPCEGEARETKACKKDACPINGGWGPWSP
WDICSVTCGGGVQKRSRLCNNPAPQFGGKDCVGDVTENQICNKQDCPIDG
CLSNPCFAGVKCTSYPDGSWKCGACPPGYSGNGIQCTDVDECKEVPDACF
NHNGEHRCENTDPGYNCLPCPPRFTGSQPFGQGVEHATANKQVCKPRNPC
TDGTHDCNKNAKCNYLGHYSDPMYRCECKPGYAGNGIICGEDTDLDGWPN
ENLVCVANATYHCKKDNCPNLPNSGQEDYDKDGIGDACDDDDDNDKIPDD
RDNCPFHYNPAQYDYDRDDVGDRCDNCPYNHNPDQADTDNNGEGDACAAD
IDGDGILNERDNCQYVYNVDQRDTDMDGVGDQCDNCPLEHNPDQLDSDSD
RIGDTCDNNQDIDEDGHQNNLDNCPYVPNANQADHDKDGKGDACDHDDDN
DGIPDDKDNCRLVPNPDQKDSDGDGRGDACKDDFDHDSVPDIDDICPENV
DISETDFRRFQMIPLDPKGTSQNDPNWVVRHQGKELVQTVNCDPGLAVGY
DEFNAVDFSGTFFINTERDDDYAGFVFGYQSSSRFYVVMWKQVTQSYWDT
NPTRAQGYSGLSVKVVNSTTGPGEHLRNALWHTGNTPGQVRTLWHDPRHI
GWKDFTAYRWRLSHRPKTGFIRVVMYEGKKIMADSGPIYDKTYAGGRLGL
FVFSQEMVFFSDLKYECRDP The underlined N in the first line of the sequence above refers to amino acid number 1 of the mature protein (i.e., without the 18- to 22-residue signal peptide sequence, here assumed to be 18 residues; see p. 13 and FIG. 1 in Adams J C et al. *The Thrombospondin Gene Family*, 1995).

Here is a partially annotated version of the human TSP-1 sequence from GenBank, broken into domains, and including indications of some of the functional regions that have been identified in the literature.

MGLAWGLGVLFLMHVCGT (SEQ ID NO: 39) [The signal peptide is considered to be 18-22 residues long (18 residues assumed here, following *The Thrombospondin Gene Family* by J C Adams et al. 1995)]

<u>N</u>RIPESGGDNSVFDIFELTGAA<u>RKGSGRRL</u>VKGPDPS SPAFRIEDANLIPPVPDDKFQDLVDAVRAEKGFLLL ASL<u>RQMKKT</u>RGTLLALERKDHSGQVFSVVSNGK AGTLDLSLTVQGKQHVVSVEEALLATGQWKSITL FVQEDRAQLY<u>IDCEKMENAELD</u>VPIQSVFTRDLAS TARLRIAKGGVNDNFQGVLQNVRFVFGTTPEDIL RNKGCSSSTSVLLTLDNNVVNGSSPAIRTNY (SEQ ID NO: 40) [N-terminal domain (I-240). The underlined N at the beginning of this domain refers to amino acid number 1 of the mature protein (i.e., without the 18- to 22-residue signal peptide sequence, here assumed to be 18 residues; see p. 13 and FIG. 1 in Adams J C et al. *The Thrombospondin Gene Family*, 1995). Two apparent heparin-binding regions are double-underlined. Finally, the last underlined region in this domain corresponds to "synthetic peptide N12/I encompassing amino acid residues 151-164 of the N-terminal domain of TSP-1", which was reported to bind fibrinogen.]

IGHKTKDLQAICGISCDELSSM (SEQ.ID NO: 41)[Domain of inter-chain disulfide bonds (241-262)]

VLELRGLRTIVTTLQDSIRKVTEENKELANELRRPPL CYHNGVQYRNNEEWTVDSCTECHCQNSVTICKK VSCPIMPCSNATVPDGECCPRCWPSDSA [(SEQ ID NO: 42) [Procollagen homology domain (263-360). Notice that the collagen V-binding region (valine[333] to lysine[412]), which is double underlined here, is partly in this domain and partly in the first type 1 repeat, which immediately follows this domain.]

DDGWSPWSEWTSCSTSCGNGIQQRGRSCDSLNNRC EGSSVQTRTCHIQECDKRFKQDGGWSHWSPWSSC SVTCGDGVITRIRLCNSPSPQMNGKPCEGEARETK ACKKDACPTNGGWGPWSPWDICSVTCGGGVQKR SRLCNNPAPQFGGKDCVGDVTENQICNKQDCPT (SEQ ID NO: 43) [Domain of type 1 repeats (361-530). This domain consists of three type 1 repeats. The double-underlined segment at the beginning of this domain is the continuation of the collagen V-binding region (valine [3331] to lysine[412]).]

DGCLSNPCFAGVKCTSYPDGSWKCGACPPGYSGNG IQCTDVDECKEVPDACFNHNGEHRCENTDPGYNC LPCPPRFTGSQPFGQGVEHATANKQVCKPRNPCTD GTHDCNKNAKCNYLGHYSDPMYRCECKPGYAGN GIICGE (SEQ ID NO: 44) [Domain of type 2 repeats (531-673). This domain consists of three type 2 repeats.]

DTDLDGWPNENLVCVANATYHCKK (SEQ ID NO: 45) [Region between the type 2 and the type 3 repeat (674-697)]

DNCPNLPNSGQEDYDKDGIGDACDDDDDNDKIP DDR (SEQ ID NO: 46)

DNCPFHYNPAQYDYDRDDVGDRC (SEQ ID NO: 47)

DNCPYNHNPDQADTDNNGEGDACAADIDGDGIL NER (SEQ ID NO: 48)

DNCQYVYNVDQRDTDMDGVGDQC (SEQ ID NO: 49)

DNCPLEHNPDQLDSDSDRIGDTCDNNQDIDEDGHQ NNL (SEQ ID NO: 50)

DNCPYVPNANQADHDKDGKGDACDHDDDNDGIP DDK (SEQ ID NO: 51)

DNCRLVPNPDQKDSDGDGRGDACKDDFDHDSVP DID (SEQ ID NO: 52) [Domain of type 3 repeats (698-925). This domain consists of seven type 3 repeats.]

DICPENVDISETDFRRFQMIPLDPKGTSQNDPNWV VRHQGKELVQTVNCDPGLAVGYDEFNAVDFSGT FFINTERDDDYAGFVFGYQSSSRFYVVMWKQVT QSYWDTNPTRAQGYSGLSVKVVNSTTGPGEHLR NALWHTGNTPGQVRTLWHDPRHIGWKDFTAYR WRLSHRPKTGFTRVVMYEGKKIMADSGPIYDKT YAGGRLGLFVFSQEMVFFSDLKYECRDP (SEQ ID NO: 53) [C-terminal domain (926-1152)]

It is understood that genetic variants of thrombospondin exist, including but not limited to human polymorphisms (e.g., see dbSNP:2229364, dbSNP:2228261, dbSNP: 2292305, dbSNP:2228262, and dbSNP:2228263 for variants in the coding region; and dbSNP:1051442, dbSNP:3743125, dbSNP:3743124, dbSNP:1051514, dbSNP:1131745, and dbSNP:11282 for 3' UTR variants). The current invention contemplates assays that detect polymorphic variants as well as common types involving the coding region, either through the use of an antibody or antibodies or other binding molecule or molecules that recognize variant and common peptide sequences, and/or through the use of sequences that are not polymorphic. It is understood that A-505 [alanine(505)] in the GenBank sequence NM_003246 is instead given as a T [threonine(505)] in FIG. 2.2a of Chapter 2, "The primary structure of the thrombospondins" in *The Thrombospondin Gene Family* by J C Adams, R P Tucker, & J Lawler, Springer-Verlag: New York, 1995, p. 16.

It is believed that the collagen type V binding domain corresponds to the region extending from valine(333) and lysine(412) of thrombospondin-1 (Takagi T et al. J Biol Chem 268:15544-15549, 1993; here, the residue numbers refer to the mature protein). Thus, the collagen type V-binding region would include a portion of the procollagen homology region of thrombospondin and all or nearly all of the first type 1 repeat of thrombospondin (see Chapter 2, "The primary structure of the thrombospondins" in *The Thrombospondin Gene Family* by J C Adams, R P Tucker, & J Lawler, Springer-Verlag: New York, 1995, pp. 11-42, but especially p. 24). See FIG. 1 of this application, as well as the annotated TSP sequence, above. As indicated on the FIG. 1 of this application, the leftmost rectangle represents the N-terminal domain (mature residues 1 to ~240), which contains heparin-binding sequence; the short vertical lines represent Cys(252) and Cys(256) of human thrombospondin-1, which are involved in inter-chain disulfide bonds, to form trimers; the first oval represents the procollagen homology domain (residues 263-360); the three slanted ovals represent the three type 1 repeats (residues 361-530), which resemble properidin and a malarial protein; the three tall ovals represent the three type 2 repeats (residues 531-673), which show similarities to the epidermal growth factor (EGF) repeat; there is a short sequence (residues 674-697) separating type 2 and type 3 repeats; the seven ovals represent the seven type 3 repeats (residues 698-925), which are rich in aspartic acid and resemble the calcium-binding pocket of parvalbumin or calmodulin; and right-hand square represents the C-terminal cell-binding domain (residues 926 to the end, that is, Proline-1152; see FIG. 2.2a in Adams J C et al. *The Thrombospondin Gene Family*, 1995, p. 16). The two chymotryptic fragments (70- and 50-kDa), and to some extent the 120-kDa tryptic fragment, indicated schematically on FIG. 1, correspond to the protease-resistant central core domain of thrombospondin.

Examples of cancers that can be detected using assays for the thrombospondin fragments include but are not limited to: adenoma, adenocarcinoma, carcinoma, lymphoina, leukemia, sacrcoma, solid cancer, liquid cancer, metastatic cancer, pre-metastatic cancer, non-metastatic cancer, a cancer with vascular invasion, internal cancer, skin cancer, cancer of the respiratory system, cancer of the circulatory system, cancer of the musculoskeletal system, cancer of a muscle, cancer of a bone, cancer of a joint, cancer of a tendor or ligament, cancer of the digestive system, cancer of the liver or biliary system, cancer of the pancreas, cancer of the head, cancer of the neck, cancer of the endocrine system, cancer of the reproductive system, cancer of the male reproductive system, cancer of the female reproductive system, cancer of the genitourinary system, cancer of a kidney, cancer of the urinary tract, cancer of a sensory system, cancer of the nervous system, cancer of a lymphoid organ, a blood cancer, cancer of a gland (for example but not limited to cancer of a mammary or a prostate gland), cancer of an endometrial tissue, cancer of a mesodermal tissue, cancer of an ectodermal tissue, cancer of an endodermal tissue, a teratoma, a poorly-differentiated cancer, a well-differentiated cancer, and a moderately differentiated cancer.

One of the options for tests for the presence of thrombospondin fragments is to fractionate the material (e.g., plasma) into fractions (e.g., positions on an electrophoresis gel, or chromatographic elution samples) collected by a technique capable of separating the fragments from thrombospondin (e.g., by electrophoresis, size-dependent chromatography, and/or affinity chromatography) and to detect the fragments in the fractions where such fragments would be expected to appear. Another of the various additional known options for assays is to test the ability of plasma to inhibit the binding of thrombospondin fragments or portions thereof to compounds (e.g., antibodies) that specifically bind to them.

Figure 3:
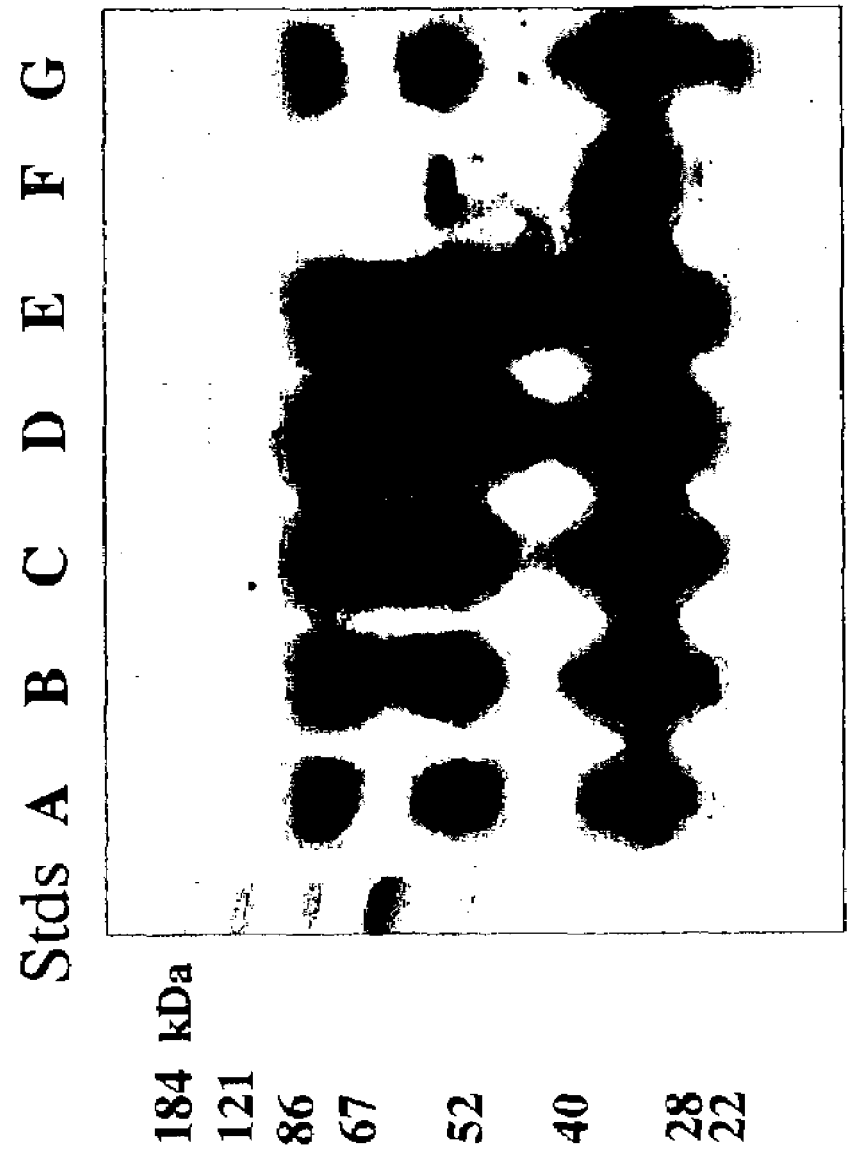
FIG. 3. Results of Western Blot analysis using TSP Ab-4 antibody and fluorescence detection. Lanes, left to right are in the sequence: a lane with the molecular weight standards (Stds), followed by samples A to G, which correspond to aliquots of the same samples as in FIG. 2.
Figure 4:
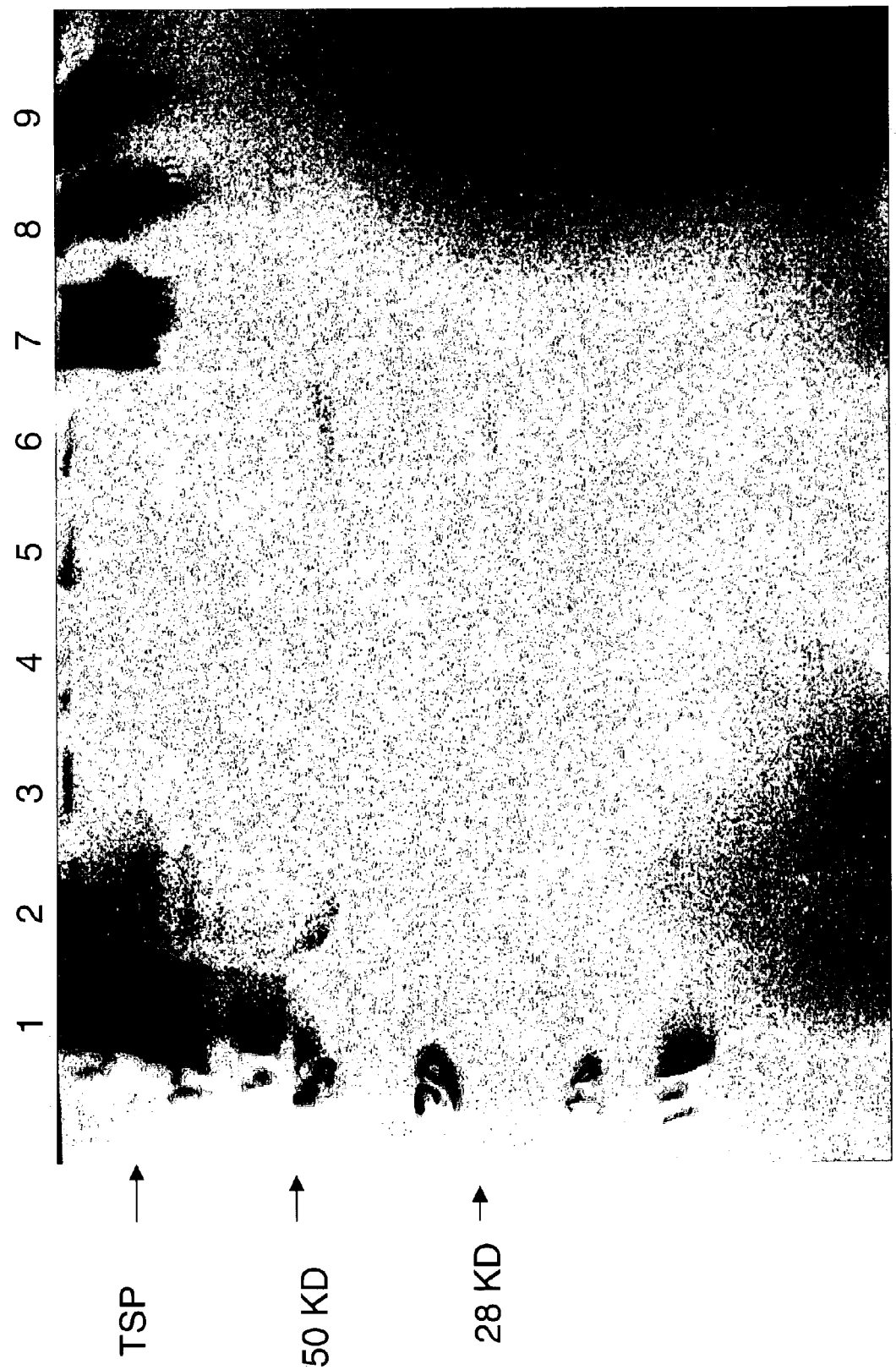
FIG. 4. Analysis of the same samples as for FIG. 3, using urea denaturation before electrophoresis, followed by electrophoresis through a 12% acrylamide gel and enzymatic colorometric detection after blotting.

The thrombospondin fragments of primary interest in the diagnostic tests are ones that have apparent molecular weights of ~85 kDa (or ~90 kDA), ~50 kDa, and ~30 kDa as determined by SDS-PAGE electrophoresis after reduction (see FIGS. 3 and 4). Preferred conditions for determining the molecular weights are those referred to below as "Standard Gel Electrophoresis Protocol." The assignment of a number such as 50 kDa to the size of a fragment reflects its approximate molecular weight as determined using the Standard Gel Electrophoresis Protocol.

It is believed that the ~85 kDa, ~50 kDa, and ~30 kDa fragments all contain an immunogenic portion of "collagen type V-binding domain" of thrombospondin. In a preferred aspect of the invention, the fragments are detected by antibody that binds to such a domain, as is believed to be the case for the TSP Ab-4 monoclonal antibody referred to below. Because the collagen V-binding domain is relatively small (~19 kDa; see Takagi et al. JBC 1993), it is concluded from the apparent molecular weights of these fragments, which are substantially greater than 19 kDa, that additional portions of the thrombospondin molecule must also be present in these fragments (multimers of the 19-kDa region are not a plausible explanation for the higher molecular weights, because the 19-kDa region does not comprise the region of inter-chain disulfide bonds, plus the fact that the gels in FIGS. 3 and 4 were run under reducing conditions). It is believed that additional portions come from the protease-resistant central core domain of thrombospondin, which can be selected from the group of thrombospondin domains consisting of the region of inter-chain disulfide bonds, the procollagen-like domain, a type 1 repeat, and to some extent a type 2 repeat and a type 3 repeat (see Prater C A et al. The properdin-like type 1 repeats of human thrombospondin contain a cell attachment site. J Cell Biol. 1991 Mar; 112 (5): 1031-40; Schultz-Cherry S et al. The type 1 repeats of thrombospondin 1 activate latent transforming growth factor-beta. J Biol Chem. 1994 Oct 28; 269 (43): 26783-8; FIG. 6.2 in Adams J C et al. The Thrombospondin Gene Family, 1995, p. 107; and chymotryptic and tryptic fragments of thrombospondin indicated schematically in FIG. 1 of this application). See also the sequence ranges given earlier in this Application. Note that several aforementioned peptides, such as, CNSPSPQMNGKPCEGEAR (SEQ ID NO: 8) (residues 444-461), RKVTEENKELANELRPP (SEQ ID NO: 9) residues 281-297) ; PQMNGKPCEGEAR (SEQ ID NO: 11) (residues 449-461); CEGEAR (SEQ ID NO: 12) (residues 456-461; and RKVTEENKE (SEQ ID NO: 13) (residues 281-289) are within the protease-resistant central core domain. An antibody against a region outside of a collagen V-binding domain, but present in a thrombospondin fragment present in a cancer patient, is also preferred.

In competition assays, a sample of material (e.g., plasma) that contains thrombospondin fragment(s) and/or thrombospondin is tested for its ability to interfere with the binding of one (or more) of the fragments to a fragment-specific binding agent, preferably an antibody, such as a monoclonal antibody. Under optimal conditions, the ability of the sample to interfere with the binding of the fragment increases monotonically in relation to the amount of similarly binding fragments in the sample. Thrombospondin will also interfere with the binding, but the present inventor has discovered that thrombospondin is present in plasma in significantly smaller amounts than the fragments. In addition, competition assays are easily standardized through the use of known quantities of fragments, synthetic or otherwise, and/or through the use of molecules, such as peptides, that contain an epitope recognized by the binding agent. In one scenario, assay detection is accomplished through the use of labeled fragments and/or peptides, and addition of a sample that contains a thrombospondin fragment or addition of known quantities of an unlabeled thrombospondin fragment (as a standard) results in competition with the binding of the labeled fragments and/or peptide to the binding agent. Loss of signal upon addition of known quantities of unlabeled or differently labeled thrombospondin fragments is used to standardize the assay.

In addition to an assay of thrombospondin fragments, other examples of platelet activation assays include but are not limited to: a thromboxane assay, a B2 assay, a beta-thromboglobulin (BTG) assay, a platelet-derived growth factor assay, a fibronectin assay, a fibrinogen assay, and a platelet factor 4 assay. Each of these can be assayed by antibody-based assays, such as an ELISA or a competitive ELISA, as is well-known in the art. Platelet activation, including the formation of platelet thrombi, is also indicated by markers that include membrane constituents, such as P selectin (which can be assayed, for example, as soluble P-selectin, which is generated as an alternatively spliced form or is proteolytically released from membrane-bound P-selectin), gpV, and glycocalicin (see Gurney D el al.: A reliable plasma marker of platelet activation: Does it exist? Am J Hematol. 2002 Jun;70(2):139-44; glycocalicin is the extracellular domain of GP Ibalpha, which can be released from Gp Ib/V/IX complexes on platelets, see Baglia F A et al.: Factor XI binding to the platelet glycoprotein Ib-IX-V complex promotes factor XI activation by thrombin. J Biol Chem. 2002 Jan 18;277(3): 1662-8), as well as platelet microparticles (see Michelson A D & Furman M I: Laboratory markers of platelet activation and their clinical significance. Curr Opin Hematol. 1999 Sep;6(5):342-8; Nomura S et al.: Relationship between platelet activation and cytokines in systemic inflammatory response syndrome patients with hematological malignancies. Thromb Res. 1999 Sep 1;95(5):205-13; Nomura S et al.: Function and clinical significance of platelet-derived microparticles. Int J Hematol. 2001 Dec;74(4):397-404) and certain prostanoids. Assays of these are also well-known in the art.

Detection of Thrombospondin Fragments by Western Blot Analysis

The following protocol (Sections I, II, and III) is referred to herein as the "Standard Gel Electrophoresis Protocol" and is preferred for determining whether the size of a fragment is ~85 kDa, ~50 kDa, ~30 kDa or another size. Nevertheless, suitable alternatives for fractionating and detecting molecules and molecular fragments are well-known in the art (see numerous methods articles and texts, as well as protocols from commercial sources) and are readily applied to the current situation with appropriate modifications.

I. Sample Preparation

Protease inhibitors added:

1 µl of leupeptin solution (1 mg/ml in sterile water) is added per ml plasma 10 µl of PMSF solution (1.74 mg/ml in isopropanol) is added per ml plasma 4× sample buffer:

$dH_2O$ 4.0 ml/0.5M tris-HCl 1.0 ml/glycerol 0.8 ml/10% SDS 1.6 ml/2-mercaptoethanol 0.4 ml/0.05% bromophenol blue 0.2 ml 5 μl plasma samples are diluted with 20 μl distilled water, and 25 μl 2× sample buffer is added, followed by heating (to aid disulfide bond reduction). 10 μl of each sample mixture is then run on the gel.

In an example of an alternative to the Standard Gel Electrophoresis Procedure, to aid reduction and denaturation, blood plasma is mixed with 5% fresh mercaptoethanol and 4-6 M fresh urea and boiled for at least 5 minutes in a fume hood.

II. Electrophoresis

Gel electrophoresis is done on SDS-polyacrylamide gels (4% stacking, 10% running gel) in tris/glycine/SDS buffer (see running buffer below, pH 8.3) at 200 V/ 7-8 cm at 25° C. for 34 minutes. Alternative electrophoretic set-ups and procedures are well-known in the art and can be used (e.g., using gels of about 8%-12% acrylamide; omission of the stacking gel), but should reliably separate 185 kDa, 85 kDa, 50 kDa, and 30 kDa (these are the approximate apparent weights on a reducing gel of thrombospondin and of the three major thrombospondin fragments in plasma). Molecular weight standards were: 184 kDa, 121 kDa, 86 kDa, 67 kDa, 52 kDa, 40 kDa, 28 kDa, and 22 kDa (FIG. 3). Other molecular weight markers are suitable as well, but should include markers near to 185 kDa (the approximate weight of thrombospondin on reducing gels) and near to 85, 50, and 30 kDa (the approximate weights on reducing gel of the major thrombospondin fragments present in plasma). Suitable molecular weight standards are purchasable from a variety of commercial sources, such as Invitrogen Life Technologies.

5× running buffer pH 8.3: Tris Base 15 g/Glycine 72 g/SDS 5 g/distilled water to 1 liter The ~85-kDa thrombospondin fragment electrophoreses close to the 86 kD standard.

The ~50-kDa thrombospondin fragment electrophoreses close to the 52 kD standard.

The ~30-kDa thrombospondin fragment electrophoreses close to the 28-kDa standard.

III. Detection of the Fragments on the Gels

The fragments may be detected by the Western Blot procedure using antibodies that react with the 85 kDa, 50 kDa, and 30 kDa fragments. TSP Ab-4 antibodies from Lab Vision Corporation can be used for this purpose (as primary antibody), as can polyclonal anti-TSP antibodies (such as Ab-8, a rabbit polyclonal antibody from Lab Vision). Following standard protocols, proteins from the polyacrylamide gel are transferred to a suitable membrane, unoccupied protein-binding sites of the membrane are then blocked (e.g., by incubation with skim milk), and the membrane is exposed to primary antibody. The presence of TSP Ab-4 antibodies that have bound to thrombospondin or thrombospondin fragments on the membrane can be detected by reacting those antibodies with fluorophore-labeled antibodies against mouse IgG (secondary antibody, i.e., that themselves react with the TSP Ab-4 antibodies), followed by subsequent fluorescence-based scanning of the membrane. Detection of polyclonal anti-TSP antibodies is performed similarly, using appropriate secondary antibodies. Other systems for detection of primary antibody are well-known in the art, including but not limited to other systems for labeling a secondary antibody, such as conjugation to an enzyme, such as horseradish peroxidase. Biotin-avidin systems are also well-known in the art, as are radioactive labeling methods.

Determination of Albumin Concentration in Plasma Samples for Purposes of Normalizing the Western Blot Results.

Gels are run under the same conditions as for the Western Blot, but then stained with Coomasie Blue. The major band (which is near the 67-kDa standard) is albumin, which is quantitated by densitometric scanning.

Illustrative, but Not Restrictive, Examples of Quantitative Assays for TSf (i.e., a Thrombospondin Fragment or Fragments):

Enzyme-linked immunoabsorbant assays (ELISA) and related approaches are well-known in the art (for an example of an ELISA of thrombospondin, but not directed towards thrombospondin fragments, see Tuszynski, G. P., Switalska, H. I., and Knudsen, K.: Modern Methods in Pharmacology in "Methods of Studying Platelet-Secreted Proteins and the Platelet Cytoskeleton," Vol. 4, Alan R. Liss, Inc., New York, p.267-286, 1987). Two types of ELISAs are competitive ELISAs, which require only one anti-TSf antibody, and sandwich ELISAs, which can require two anti-TSf antibodies. Essentially identical assays are also contemplated, in which a binding agent other than an antibody is used.

For a competitive ELISA or ELISA-like assay, two sets of wells can be used, one a set of reaction wells and the other a set of pre-mix wells. In the reaction wells, antigen is bound to a surface, such as a plate or a bead (for simplicity, the rest of this description refers to such a surface as a plate or a well, but it is understood that other surfaces can also be used). Here, the antigen would be based on a thrombospondin fragment present in a cancer patient. Said antigen could take a form selected from the group consisting of thrombospondin (TSP) itself, a TSP fragment found in a cancer patient, a TSP fragment that contains a TSP fragment found in a cancer patient, a TSP fragment that is contained within a TSP fragment found in a cancer patient, a peptide that contains an epitope from a TSP fragment in a cancer patient (where said peptide can be synthetic), and a derivatized peptide and/or fragment. The essential requirement for the fragment, protein or peptide coated on the walls is that it can compete with the TSP fragment of interest (for example a fragment in a patient's plasma) for binding to a binding agent, such as an antibody, used in the ELISA. As an illustration, TSP itself can be used, as stated above. TSP can be prepared by activating platelets in vitro (which then release TSP-1), followed by purification of this TSP from the platelet-conditioned medium; if standard 96-well microtiter plates are used, 75 ng of TSP-1 in 200 μL of phosphate-buffered saline can be added per well. Corresponding amounts (molar or mass) of TSP fragments and/or peptides can be used instead, and are preferable, based on ease of preparation and standardization. After binding the antigen to the immobilized surface, additional binding sites on the surface are blocked by standard protocols (for example, incubation with bovine serum albumin then Tween, both in phosphate-buffered saline).

The premix wells are prepared with no antigen, but then blocked (e.g., with BSA then Tween). These premix wells can be used as convenient reaction vessels for the initial binding of anti-TSf antibody with either known amounts of antigen in solution (for a standard curve) or unknown amounts of antigens in a sample to be tested (see the next two paragraphs).

In order to generate a standard curve, to the pre-mix wells are added different concentrations of a standard antigen in solution. The standard antigen might (as described elsewhere herein) be selected so as to quantitate the amount of thrombospondin fragments of the invention, the amount of a subset of thrombospondin fragment or fragments, the amount of thrombospondin, or their combined total. The antigen may be synthetic, isolated from a cancer patient, isolated from an individual without cancer, or isolated from any other appropriate source, including but not limited to recombinant material. As indicated above, the immobilized antigen in the reaction wells and the antigen in solution in the pre-mix wells do not have to be the same, but they should both react with—and thereby eventually compete for—the binding agent (such as a primary antibody) used in the assay. As an illustrative example, if TSP-1 itself is the standard antigen in solution in the premix wells, 0, 2, 5, 10, 20, 40, 60, and 80 ng can be added per well, in PBS-Tween, in volume of 110 uL per microtiter well. Corresponding amounts (molar or mass) of TSP fragments or peptides can be used instead, and are preferable, based on their ease of preparation and standardization. These wells will be used to generate a standard curve.

Unknowns (i.e., samples in which it is desired to quantitate the concentration of a TSP fragment) are also added, to separate pre-mix wells. For plasma samples, it is typical to dilute them beforehand, say, with PBS-Tween. This can be important, to bring the amount of TSf down into the range of the standard curve, and also to dilute potentially interfering substances in plasma (one such interfering substance may be fibrinogen, which can bind TSP and some TSP fragments). Total volume should be the same as for the soluble antigen standards. Diluted binding agent, such as an antibody (e.g., in 110 uL), that reacts against a TSP fragment found in a cancer patient is then added. Note that the antigen immobilized in the reaction wells and the antigen in solution in the pre-mix wells must be chosen to also react against this binding agent. An incubation is performed, to allow antigen-antibody binding (or target-binding agent binding) to occur in the pre-mix wells.

An aliquot (e.g., 200 uL) of liquid from each premix well (standards and unknowns) is then transferred to an antigen-coated reaction well, followed by an incubation (as a blank, some wells can receive buffer only, such as PBS-Tween). After this incubation, liquid is removed from the antigen-coated reaction wells, and the wells are washed. If a primary antibody is used as the binding agent, enzyme-conjugated secondary antibody (specific against the primary antibody) is then added to the wells, followed by an incubation to allow it to bind to whatever primary antibody has bound to the immobilized TSf on the plate. This step is followed by detection (for example, if the secondary antibody is conjugated to alkaline phosphatase, detection can be accomplished with Sigma phosphatase substrate followed by absorbance readings at 405 nm). A standard curve is plotted, and quantities of a TSf in the unknown samples are calculated based on the standard curve. Note that higher amounts of TSf in the sample will result in less primary antibody bound to the immobilized antigen on the well, and hence less signal from the secondary antibody. Similar detection methods are used if the binding agent is a non-antibody.

Sandwich ELISAs and ELISA-like assays are also contemplated. In this case, a first anti-TSf antibody (or a first non-antibody binding agent that binds TSf) is immobilized on a plate, a bead, or another surface, and it is used to capture the TSf in a standard or unknown sample. The first antibody is often polyclonal, but this is not a requirement. Detection of captured material is then accomplished with a second anti-TSf antibody. The second antibody is often monoclonal, but this is not a requirement. As is well-known in the art, the first and second antibodies should not substantially interfere with each other's access to the captured material. Detection can be accomplished with an enzyme-linked antibody specific to the second anti-TSf antibody. Again, if the first (capturing) binding agent and/or the second (detecting) binding agent is a non-antibody, similar methods are used.

Many variants well-known in the art are contemplated for these competitive and sandwich ELISAs and ELISA-like assays. For example, non-enzymatic methods, such as radioactive, fluorescent, biotin-avidin-based methods, and other methods to detect the anti-TSf antibody are contemplated. Also, automated assays, such as ones performed on a clinical autoanalyzer, are contemplated. Also, various anti-TSf antibodies are contemplated, including but not limited to polyclonal antibodies, monoclonal antibodies, anti-peptide antibodies, antibodies against a TSP fragment present in a cancer patient, antibodies against a TSP fragment generated in vitro, and antibodies against a TSP fragment generated in vitro by proteolysis. Single-chain antibodies are also contemplated, as are non-antibodies.

For the sandwich ELISA, one option is the use of color-coded microbeads (micro spheres) with immobilized anti-TSf antibody to capture, then a fluorescent second anti-TSf antibody to detect. The detection apparatus reads each bead, one at a time, assaying for bead color as well as the signal from the second anti-TSf antibody. The advantage here is that several different analytes can be assayed at once, such as one group of beads for full-length TSP (or an epitope outside of what circulates in substantial concentration in a cancer patient) and another group of beads, of a different color, for a TSP fragment. Or, one group of beads to assay an epitope present in the ~85-kDa TSP fragment that is not present in the ~50- or ~3-kDa fragments, and another group of beads to assay an epitope present in the ~50-kDa fragment but not the ~30-kDa fragment (this is followed by a numerical calculation to yield the amounts of ~85-kDa fragment and of ~50-kDa fragment separately). An example of this use of color-coded beads can be found at the web site for Linco Research, Inc.

Another option for analyzing multiple analytes is Search-Light™ Proteome Arrays, which are multiplexed sandwich ELISAs, currently adapted for the quantitative measurement of two to 16 proteins per well. It is understood herein that the method can also be used for protein fragments, such as one or more thrombospondin fragments. Using a spotting technique, 2 to 16 target-specific antibodies are bound to each well of a microplate, although it is understood that this number can be expanded with improved spotting techniques and/or larger wells. Following a standard sandwich ELISA procedure, luminescent signals are imaged with a cooled CCD (charged coupled device) camera. The image is then analyzed using Array Vision™ software. The amount of signal generated at each spot is related to the amount of target protein in the original standard or sample. Values for specific proteins and/or protein fragments can be calculated based on the position of the spots and comparison of density values for unknowns to density values for known standards (and TSP fragments or peptides can be used as standards). The SearchLight™ technology is available through Pierce Boston Technology Center, including customized arrays using proprietary reagents from outside Pierce or assay targets not currently available at Pierce.

Other assay methods are also contemplated. Immunoturbidimetric assays are contemplated (for a detailed example of this approach with another plasma protein, see Levine, D. M. and Williams, K. J.: Automated measurement of mouse apolipoprotein B: convenient screening tool for mouse models of atherosclerosis. *Clin. Chem.* 43:669-674, 1997), as well as turbidimetric assays that use binding agents in general. Other competitive assays are also contemplated, such as ones in which material in standards and an unknown competes with one or more labeled peptides, one or more labeled TSP fragments, and/or labeled TSP for binding to an agent that binds TSf, such as an anti-TSf antibody (the label is then used for detection and hence quantitation). One example of this approach is to immobilize an anti-TSf antibody, and then add sample mixed with labeled peptide, labeled TSP fragments, or labeled TSP, so that sample and labeled material compete for binding to the immobilized antibody (note that this approach requires only one anti-TSf antibody). Binding of labeled material is then quantitated. It is understood that any of these assays, including immune-based and non-immune-based assays, can be automated. It is also understood that potentially interfering substances in unknown samples can be diluted, removed, inhibited, avoided (for example, in the case of fibrinogen, by using epitopes away from a fibrinogen-binding region of TSP), and/or compensated for.

Use of Thrombospondin Fragments as Immunogens to Generate Fragment-Specific Antibodies:

A purified preparation of fragments (e.g., by elution of fragments from the gel, by immunoprecipitation or antibody column or other immune-based purification methods, by recombinant DNA techniques, by chemical synthesis, or by a combination of synthesis and/or purification methods) is injected into a rabbit or rabbits with any of the standard adjuvants used with peptide immunogens and antibodies are collected using protocols well known in the art. For small peptides, linkage to a carrier, such as keyhole limpet hemocyanin or bovine serum albumin, is well-known in the art. Injection into other animals is also well-known, including but not limited to a goat, sheep, chicken, turkey, donkey, dog, cat, rat, and mouse. Monoclonal antibodies can be prepared using antibody-producing cells obtained from any immunized animal, but the technology is most easily available for the mouse (for example, antibody-producing cells from an immunized animal are fused with an immortal cell, then clones of fused cells are screened for their production of antibody against one or more thrombospondin fragments of interest).

It is understood that the methods disclosed herein are readily applied to other members of the thrombospondin gene family, including but not limited to TSP-2 (for a description of the thrombospondin gene family, see *The Thrombospondin Gene Family* by J C Adams, R P Tucker, & J Lawler, Springer-Verlag: New York, 1995; de Fraipont F et al. *Trends Mol. Med.*, 7:401-407, 2001; and elsewhere). It is also understood that the methods disclosed herein are readily applied to other animal species of economic and/or emotional importance, including but not limited to pets, animals used in breeding, racehorses, and racing dogs.

EXAMPLES

Western Blot Analysis of Plasma Samples from Cancer Patients

Electrophoresis was done according to the Standard Gel Electrophoresis Protocol described above.

Table I shows plasma and serum samples obtained for analysis.

TABLE 1

| Sample | Plasma/Serum | Cancer | Stage/Grade | Age/Sex | Comment |
|---|---|---|---|---|---|
| A | plasma | colon T2 | I/G2 | 57/F | Ascending |
| B | plasma | colon T3 | II/G2 | 71/M | Ascending |
| C | plasma | prostate | II/Gleason 6 | 71/M | DRE-abnormal |
| D | plasma | prostate | II/Gleason 5 | 63/M | DRE-abnormal |
| E | plasma | lung T2 | IB/G2 | 67/M | Squamous |
| F | serum | | | | TSP is released from platelets during clotting, and proteases are activated during clotting. |
| G | plasma | no cancer | N/A | F | lichen planus, a non-cancerous inflammatory disorder |

Figure 2:
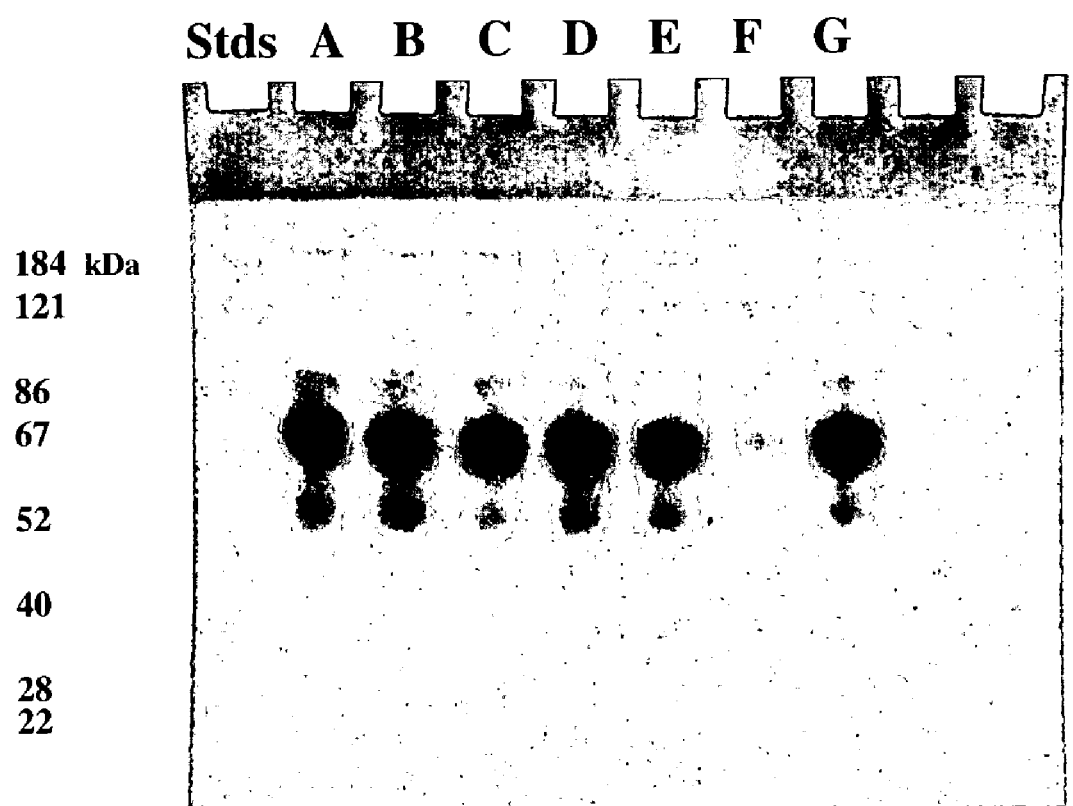
FIG. 2. Results of staining a gel with Coomasie Blue. Lanes, left to right are in the sequence: a lane with the molecular weight standards (Stds), followed by samples A to G.

The results are shown in FIGS. 2 and 3, and the quantitative data are summarized in Table 2.

TABLE 2

| | Quantitation of thrombospondin fragments, normalized for sample loading | | | | | | |
|---|---|---|---|---|---|---|---|
| Approx MW (kDa) | A Colon-1 | B Colon-2 | C Prostate-1 | D Prostate-2 | E Lung | F Serum | G No cancer |
| 85 | 0.572 | 0.847 | 1.175 | 1.292 | 1.142 | 1.434 | 0.526 |
| | 108.8% | 161.1% | 223.6% | 245.7% | 217.4% | 272.9% | 100.0% |
| 50 | 0.534 | 0.666 | 1.037 | 1.416 | 1.809 | 2.722 | 0.596 |
| | 89.7% | 111.8% | 174.0% | 237.7% | 303.6% | 456.9% | 100.0% |
| 30 | 1.210 | 1.401 | 1.687 | 1.593 | 1.988 | 7.351 | 1.424 |
| | 85.0% | 98.4% | 118.5% | 111.9% | 139.6% | 516.3% | 100.0% |
| Total Ab4 signal | 2.316 | 2.914 | 3.898 | 4.301 | 4.939 | 11.507 | 2.545 |
| | 91.0% | 114.5% | 153.2% | 169.0% | 194.1% | 452.1% | 100.0% |
| Albumin signal above bkg | 24020 | 26723 | 25187 | 27073 | 23888 | 4359 | 26110 |

Numbers refer to the strengths of TSf signal from the Western blot (FIG. 3), normalized to the albumin signal from Coomassie staining (FIG. 2 and final row of numbers in this Table). Percentages indicate the ratio to the no-cancer sample (sample G).

The results summarized in Table 2 represent data generated by densitometric scanning of the photographic film generated by fluorescent staining of the TSP Ab-4 Western Blot (See FIG. 3). Thus, for very dark signals, such as the band or group of bands around 30 kDa, the fact that the signals on film saturate when very strong means that increases compared to the no-cancer control sample are seriously under-estimated. This is not particularly evident in the serum sample, which served as the positive control for increased signal, owing to platelet activation (much less serum was loaded, as is evident from the albumin signal; so even though it generated a strong normalized signal, it did not saturate the film nearly as much).

To obtain the data for Table 2, the signal (above background) for the Western Blot was determined and that signal was normalized to the albumin signal (above background) for the gel shown in FIG. 2. Table 2 shows the normalized signal (e.g., 0.572) with the percentage (e.g., 108.8%) underneath the normalized signal being the percentage of the "no-cancer" signal.

The molecular weight standards used were 184 kDa, 121 kDa, 86 kDa, 67 kDa, 52 kDa, 40 kDa, 28 kDa, and 22 kDa. Based on the given molecular weights and the relative positions of the standard bands versus the TSP Ab-4 bands and groups of bands, it was concluded that the TSP Ab-4 signals were in three general bands or groups of bands, at approximately 85, 50, and 30 kDa (see FIG. 3). Notice, for example, the relative strength of signals at around 185 kDa (thrombospondin) versus around 85, 50, and 30 kDa (fragments). It is clear that there is overwhelmingly more signal from the fragments than from thrombospondin itself. Thus, detection of specific fragments, as disclosed in the current inventions, is preferred over detection of the TSP molecule itself, or general detection of epitopes that occur throughout the whole TSP molecule, or detection of epitopes outside of those contained within the specific fragments demonstrated herein.

The plasma samples from cancer patients (lanes A-E) came from Golden West Biologicals, Inc. of Temecula, Calif. The serum sample (lane F) was from a non-cancerous individual. The no-cancer control plasma (lane G) came from an individual with lichen planus, a non-cancerous but inflammatory skin condition.

The serum sample (Lane F) was prepared by deliberately clotting the blood. Protease inhibitors were not added to sample F until after clotting had been completed and the serum had been harvested. Ideally for the current invention, however, blood is not allowed to clot during sample collection (activation of platelets during clotting causes release of thrombospondin, which was used here on purpose to increase the signal from sample F), and protease inhibitors are added promptly during sample collection (not done for sample F because the clotting cascade involves activation of proteases).

The predominance of thrombospondin fragments, as opposed to thrombospondin itself, in sample F is consistent with a) platelet activation and release of thrombospondin, plus b) activation of proteases of the clotting cascade, which evidently cleaved the newly released thrombospondin.

Plasma samples from Golden West Biologicals were samples from individuals with relatively early disease. The first colon cancer sample (lane A) was from an individual with stage 1, grade G2 disease. All other cancer samples (lanes B-E) came from individuals with stage II disease (except for lane E, which was stage IB). Plasma from patients with such relatively early stage cancers would be expected to have a lower concentration of thrombospondin fragments than plasma from patients with more advanced cancers. Nevertheless, the robustness of the technique is demonstrated by the fact that (1) increased levels were found with the earlier stage cancers, and (2) gel scanning was done under conditions in which portions of the detecting film were saturated or nearly saturated.

All cancer samples show an increased signal from the 85-kDa band (or group of similarly electrophoresing bands). All but the stage I sample show increased signal from the 50-kDa band (or group of bands), as well as increased total Ab-4 signal. All but the two early colon cancer samples show increased signal from the 30-kDa band (or group of bands). Thus, the detection and quantitation of specific thrombospondin fragments works to distinguish even relatively early cancer patients from a no-cancer control who has a non-cancerous disease. These thrombospondin fragments are well-suited for diagnostic assays because (a) they have specific molecular weights (or molecular weight ranges); and (b) they contain specific epitopes. The present results provide validation for other fragment-based approaches, including (but not limited to) non-competitive ELISA and ELISA-like assays, and competition assays.

FIG. 4 shows the results of an independent gel analysis of the samples. The samples were denatured then run on a 12% gel, transblotted, and then stained with the same TSP Ab-4 that we used before. Unlike the blot shown in FIG. 3, the denaturation step here included urea, and detection used an enzymatic colorimetric method that is based on horseradish peroxidase conjugates and the BioRad Opti-4CN substrate kit, not fluorescence as before. Along the left edge of lane 1, there are from top to bottom, the following handwritten numbers evident: 1, 97, 66, 45, 30, 20, and 14, respectively. With the exception of 1, the numbers correspond to the positions where standard proteins of corresponding molecular weights (in kDa) had electrophoresed.

In FIG. 4, Lanes 2 through 6 correspond to patients A though E, respectively, in Table 1. Lanes 1 and 7 through 9 show the electrophoresis patterns of thrombospondin. The results confirm that:

a) there is virtually no TSP in the plasma samples (the first plasma lane shows some TSP at its appropriate monomer molecular weight, but this is certainly spill-over from the vastly overloaded first sample lane);

b) there are indeed TSP fragments in the plasma samples; and c) the fragments have molecular weights of about 28, 50, and a faint band around 90 kDa. In this blot, the TSf bands are very sharp, implying well-defined molecular weight fragments (presumably a purely technical improvement, owing to better denaturation in the presence of urea). As in FIG. 3, there are a number of less prominent fragment bands at other molecular weights. It is understood that a thrombospondin fragment in any of these bands can also be assayed and used in diagnosis and screening and in kits.

The invention claimed is:

1. A method to detect the presence and/or clinical course of a neoplastic disease in an individual, wherein the method comprises the steps of:
   (1) obtaining a plasma sample of an individual suspected of having, or known to have, a neoplastic disease;
   (2) measuring the individual's plasma level of a thrombospondin fragment or fragments;
   (3) utilizing the result of step (2) in a diagnosis as to whether the individual has a neoplastic disease such that the greater the plasma level of said thrombospondin fragment or fragments, the more likely that the diagnosis will be that a neoplastic disease is present in said individual; said fragment or fragments being at least 6 continuous amino acyl residues in length but of a molecular weight less than 110 kDa; wherein the size in kDa is that determined by gel electrophoresis after disulfide bond reduction.

2. A method of claim 1 where the individual referred to in claim 1 is a first individual and the plasma level referred to in claim 1 is the first individual's plasma fragment level and wherein the method further comprises the steps of:
   (4) measuring, in a second individual, the plasma level of the same thrombospondin fragment or fragments measured for the first individual, said second individual considered to not have neoplastic disease, the plasma level of said fragment or fragments in the second individual being the second individual's plasma fragment level;
   (5) utilizing the result of step (4) in the diagnosis of whether the first individual has a neoplastic disease; such that greater the extent to which the first individuals plasma thrombospondin fragment level exceeds the plasma thrombospondin level of the second individual, the more likely that the diagnosis will be that the first individual has a neoplastic disease.

3. A method of claim 1 further comprising the steps of assaying the individual's plasma level of a thrombospondin fragment or fragments more than once, and utilizing a change in plasma level from an older to a more recent value to indicate appearance or progression or improvement of a neoplastic disease wherein said appearance or progression is indicated by an increase in the plasma level and said improvement is indicated by a decrease in said plasma level.

4. A method of claim 1, 2, or 3, wherein the measurement of a plasma level of a thrombospondin fragment comprises the use of a binding agent, said binding agent capable of binding said fragment or fragments.

5. A method of claim 4 wherein the thrombospondin fragment or fragments are separated from thrombospondin before said fragment or fragments are bound to the binding agent.

6. A method of claims 1, 2 or 3 wherein the molecular weight of each of the fragment or fragments is at least 20 kDa, wherein the size in kDa is that determined by gel electrophoresis after disulfide bond reduction.

7. A method of claim 4 wherein the molecular weight of each of the fragment or fragments is at least 20 kDa, wherein the size in kDa is that determined by gel electrophoresis after disulfide bond reduction.

8. A method of claim 5 wherein the molecular weight of each of the fragment or fragments is at least 20 kDa, wherein the size in kDa is that determined by gel electrophoresis after disulfide bond reduction.

9. A method of claim 4 wherein the binding agent is an antibody.

10. A method of claim 5 wherein the binding agent is an antibody.

11. A method of claim 7 wherein the binding agent is an antibody.

12. A method of claim 8 wherein the binding agent is an antibody.

* * * * *

UNITED STATES PATENT AND TRADEMARK OFFICE
CERTIFICATE OF CORRECTION

| | | |
|---|---|---|
| PATENT NO. | : 7,655,411 B2 | Page 1 of 1 |
| APPLICATION NO. | : 10/419462 | |
| DATED | : February 2, 2010 | |
| INVENTOR(S) | : Kevin J. Williams | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1642 days.

Signed and Sealed this

Twenty-eighth Day of December, 2010

David J. Kappos
*Director of the United States Patent and Trademark Office*

SEQUENCE LISTING

<160> NUMBER OF SEQ ID NOS: 64

<210> SEQ ID NO 1
<211> LENGTH: 6
<212> TYPE: PRT
<213> ORGANISM: Artificial
<220> FEATURE:
<223> OTHER INFORMATION: Thrombospondin Region

<400> SEQUENCE: 1

Thr Glu Glu Asn Lys Glu
1               5

<210> SEQ ID NO 2
<211> LENGTH: 15
<212> TYPE: PRT
<213> ORGANISM: Artificial
<220> FEATURE:
<223> OTHER INFORMATION: thrombospondin Region which includes an
      N-terminal CYS added to aid conjugation

<400> SEQUENCE: 2

Cys Leu Gln Asp Ser Ile Arg Lys Val Thr Glu Glu Asn Lys Glu
1               5                   10                  15

<210> SEQ ID NO 3
<211> LENGTH: 14
<212> TYPE: PRT
<213> ORGANISM: Artificial
<220> FEATURE:
<223> OTHER INFORMATION: Thrombospondin Region

<400> SEQUENCE: 3

Leu Gln Asp Ser Ile Arg Lys Val Thr Glu Glu Asn Lys Glu
1               5                   10

<210> SEQ ID NO 4
<211> LENGTH: 6
<212> TYPE: PRT
<213> ORGANISM: Artificial
<220> FEATURE:
<223> OTHER INFORMATION: Thmbospondin Region

<400> SEQUENCE: 4

Glu Gly Glu Ala Arg Glu
1               5

<210> SEQ ID NO 5
<211> LENGTH: 14
<212> TYPE: PRT
<213> ORGANISM: Artificial
<220> FEATURE:
<223> OTHER INFORMATION: Thrombospondin Region

<400> SEQUENCE: 5

Pro Gln Met Asn Gly Lys Pro Cys Glu Gly Glu Ala Arg Glu
1               5                   10

<210> SEQ ID NO 6
<211> LENGTH: 6
<212> TYPE: PRT
<213> ORGANISM: Artificial
<220> FEATURE:
<223> OTHER INFORMATION: Thrombospondin Region -continued

```
<400> SEQUENCE: 6

Glu Asp Thr Asp Leu Asp
1               5

<210> SEQ ID NO 7
<211> LENGTH: 15
<212> TYPE: PRT
<213> ORGANISM: Artificial
<220> FEATURE:
<223> OTHER INFORMATION: Thrombospondin

<400> SEQUENCE: 7

Tyr Ala Gly Asn Gly Ile Ile Cys Gly Glu Asp Thr Asp Leu Asp
1               5                   10                  15

<210> SEQ ID NO 8
<211> LENGTH: 18
<212> TYPE: PRT
<213> ORGANISM: Artificial
<220> FEATURE:
<223> OTHER INFORMATION: Thrombospondin Region

<400> SEQUENCE: 8

Cys Asn Ser Pro Ser Pro Gln Met Asn Gly Lys Pro Cys Glu Gly Glu
1               5                   10                  15

Ala Arg

<210> SEQ ID NO 9
<211> LENGTH: 17
<212> TYPE: PRT
<213> ORGANISM: Artificial
<220> FEATURE:
<223> OTHER INFORMATION: Thrombospondin Region

<400> SEQUENCE: 9

Arg Lys Val Thr Glu Glu Asn Lys Glu Leu Ala Asn Glu Leu Arg Arg
1               5                   10                  15

Pro

<210> SEQ ID NO 10
<211> LENGTH: 18
<212> TYPE: PRT
<213> ORGANISM: Artificial
<220> FEATURE:
<223> OTHER INFORMATION: Thrombospondin Region which includes an
      N-terminal CYS added to aid conjugation

<400> SEQUENCE: 10

Cys Arg Lys Val Thr Glu Glu Asn Lys Glu Leu Ala Asn Glu Leu Arg
1               5                   10                  15

Arg Pro

<210> SEQ ID NO 11
<211> LENGTH: 13
<212> TYPE: PRT
<213> ORGANISM: Artificial
<220> FEATURE:
<223> OTHER INFORMATION: Thrombospondin Region

<400> SEQUENCE: 11

Pro Gln Met Asn Gly Lys Pro Cys Glu Gly Glu Ala Arg
1               5                   10
```

<210> SEQ ID NO 12
<211> LENGTH: 6
<212> TYPE: PRT
<213> ORGANISM: Artificial
<220> FEATURE:
<223> OTHER INFORMATION: Thrombospondin Region

<400> SEQUENCE: 12

Cys Glu Gly Glu Ala Arg
1               5

<210> SEQ ID NO 13
<211> LENGTH: 9
<212> TYPE: PRT
<213> ORGANISM: Artificial
<220> FEATURE:
<223> OTHER INFORMATION: Thrombospondin Region

<400> SEQUENCE: 13

Arg Lys Val Thr Glu Glu Asn Lys Glu
1               5

<210> SEQ ID NO 14
<211> LENGTH: 15
<212> TYPE: PRT
<213> ORGANISM: Artificial
<220> FEATURE:
<223> OTHER INFORMATION: Thrombospondin Region

<400> SEQUENCE: 14

Asp Asp Asp Asp Asn Asp Lys Ile Pro Asp Asp Arg Asp Asn Cys
1               5                   10                  15

<210> SEQ ID NO 15
<211> LENGTH: 15
<212> TYPE: PRT
<213> ORGANISM: Artificial
<220> FEATURE:
<223> OTHER INFORMATION: Thrombospondin Region additional NH2 Group

<400> SEQUENCE: 15

Asp Asp Asp Asp Asn Asp Lys Ile Pro Asp Asp Arg Asp Asn Cys
1               5                   10                  15

<210> SEQ ID NO 16
<211> LENGTH: 7
<212> TYPE: PRT
<213> ORGANISM: Artificial
<220> FEATURE:
<223> OTHER INFORMATION: Thrombospondin Region

<400> SEQUENCE: 16

Asp Asp Asp Asp Asn Asp Lys
1               5

<210> SEQ ID NO 17
<211> LENGTH: 14
<212> TYPE: PRT
<213> ORGANISM: Artificial
<220> FEATURE:
<223> OTHER INFORMATION: Thrombospondin Region

<400> SEQUENCE: 17

Asn Leu Pro Asn Ser Gly Gln Glu Asp Tyr Asp Lys Asp Gly
1               5                   10

<210> SEQ ID NO 18
<211> LENGTH: 15
<212> TYPE: PRT
<213> ORGANISM: Artificial
<220> FEATURE:
<223> OTHER INFORMATION: Thrombospondin Region plus N-terminal CYS to
      aid conjugation

<400> SEQUENCE: 18

Cys Asn Leu Pro Asn Ser Gly Gln Glu Asp Tyr Asp Lys Asp Gly
1               5                   10                  15

<210> SEQ ID NO 19
<211> LENGTH: 6
<212> TYPE: PRT
<213> ORGANISM: Artificial
<220> FEATURE:
<223> OTHER INFORMATION: thrombospondin Region

<400> SEQUENCE: 19

Glu Asp Tyr Asp Lys Asp
1               5

<210> SEQ ID NO 20
<211> LENGTH: 19
<212> TYPE: PRT
<213> ORGANISM: Artificial
<220> FEATURE:
<223> OTHER INFORMATION: Thrombospondin Region

<400> SEQUENCE: 20

Cys Pro Tyr Asn His Asn Pro Asp Gln Ala Asp Thr Asp Asn Asn Gly
1               5                   10                  15

Glu Gly Asp

<210> SEQ ID NO 21
<211> LENGTH: 15
<212> TYPE: PRT
<213> ORGANISM: Artificial
<220> FEATURE:
<223> OTHER INFORMATION: Thrombospondin Region

<400> SEQUENCE: 21

Cys Arg Leu Val Pro Asn Pro Asp Gln Lys Asp Ser Asp Gly Asp
1               5                   10                  15

<210> SEQ ID NO 22
<211> LENGTH: 8
<212> TYPE: PRT
<213> ORGANISM: Artificial
<220> FEATURE:
<223> OTHER INFORMATION: Thrombospondin region

<400> SEQUENCE: 22

Asp Gln Lys Asp Ser Asp Gly Asp
1               5

<210> SEQ ID NO 23
<211> LENGTH: 20
<212> TYPE: PRT
<213> ORGANISM: Artificial
<220> FEATURE:
<223> OTHER INFORMATION: Thrombospondin Region

```
<400> SEQUENCE: 23

Cys Pro Tyr Val Pro Asn Ala Asn Gln Ala Asp His Asp Lys Asp Gly
1               5                   10                  15

Lys Gly Asp Ala
            20

<210> SEQ ID NO 24
<211> LENGTH: 6
<212> TYPE: PRT
<213> ORGANISM: Artificial
<220> FEATURE:
<223> OTHER INFORMATION: thrombospondin Region

<400> SEQUENCE: 24

Thr Glu Arg Asp Asp Asp
1               5

<210> SEQ ID NO 25
<211> LENGTH: 15
<212> TYPE: PRT
<213> ORGANISM: Artificial
<220> FEATURE:
<223> OTHER INFORMATION: Thrombospondin Region

<400> SEQUENCE: 25

Asp Phe Ser Gly Thr Phe Phe Ile Asn Thr Glu Arg Asp Asp Asp
1               5                   10                  15

<210> SEQ ID NO 26
<211> LENGTH: 6
<212> TYPE: PRT
<213> ORGANISM: Artificial
<220> FEATURE:
<223> OTHER INFORMATION: Thrombospondin Region

<400> SEQUENCE: 26

Glu Arg Lys Asp His Ser
1               5

<210> SEQ ID NO 27
<211> LENGTH: 14
<212> TYPE: PRT
<213> ORGANISM: Artificial
<220> FEATURE:
<223> OTHER INFORMATION: Thrombospondin Region

<400> SEQUENCE: 27

Thr Arg Gly Thr Leu Leu Ala Leu Glu Arg Lys Asp His Ser
1               5                   10

<210> SEQ ID NO 28
<211> LENGTH: 15
<212> TYPE: PRT
<213> ORGANISM: Artificial
<220> FEATURE:
<223> OTHER INFORMATION: Thrombospondin Region plus N-termianl CYS

<400> SEQUENCE: 28

Cys Thr Arg Gly Thr Leu Leu Ala Leu Glu Arg Lys Asp His Ser
1               5                   10                  15

<210> SEQ ID NO 29
<211> LENGTH: 6
<212> TYPE: PRT
<213> ORGANISM: Artificial
```

```
<220> FEATURE:
<223> OTHER INFORMATION: Thrombospondin Region

<400> SEQUENCE: 29

Asp Asp Lys Phe Gln Asp
1               5

<210> SEQ ID NO 30
<211> LENGTH: 14
<212> TYPE: PRT
<213> ORGANISM: Artificial
<220> FEATURE:
<223> OTHER INFORMATION: Thrombospondin Region

<400> SEQUENCE: 30

Ala Asn Leu Ile Pro Pro Val Pro Asp Asp Lys Phe Gln Asp
1               5                   10

<210> SEQ ID NO 31
<211> LENGTH: 15
<212> TYPE: PRT
<213> ORGANISM: Artificial
<220> FEATURE:
<223> OTHER INFORMATION: Thrombospondin Region plus N-terminal CYS

<400> SEQUENCE: 31

Cys Ala Asn Leu Ile Pro Pro Val Pro Asp Asp Lys Phe Gln Asp
1               5                   10                  15

<210> SEQ ID NO 32
<211> LENGTH: 6
<212> TYPE: PRT
<213> ORGANISM: Artificial
<220> FEATURE:
<223> OTHER INFORMATION: Thrombospondin region

<400> SEQUENCE: 32

Asp Cys Glu Lys Met Glu
1               5

<210> SEQ ID NO 33
<211> LENGTH: 15
<212> TYPE: PRT
<213> ORGANISM: Artificial
<220> FEATURE:
<223> OTHER INFORMATION: Thrombospondin Region

<400> SEQUENCE: 33

Glu Asp Arg Ala Gln Leu Tyr Ile Asp Cys Glu Lys Met Glu Asn
1               5                   10                  15

<210> SEQ ID NO 34
<211> LENGTH: 17
<212> TYPE: PRT
<213> ORGANISM: Artificial
<220> FEATURE:
<223> OTHER INFORMATION: Thrombospondin Region

<400> SEQUENCE: 34

Cys Gly Thr Asn Arg Ile Pro Glu Ser Gly Gly Asp Asn Ser Val Phe
1               5                   10                  15

Asp
```

```
<210> SEQ ID NO 35
<211> LENGTH: 14
<212> TYPE: PRT
<213> ORGANISM: Artificial
<220> FEATURE:
<223> OTHER INFORMATION: Thrombospondin region

<400> SEQUENCE: 35

Asn Arg Ile Pro Glu Ser Gly Gly Asp Asn Ser Val Phe Asp
1               5                   10

<210> SEQ ID NO 36
<211> LENGTH: 19
<212> TYPE: PRT
<213> ORGANISM: Artificial
<220> FEATURE:
<223> OTHER INFORMATION: Thrombospondin Region

<400> SEQUENCE: 36

Gly Trp Lys Asp Phe Thr Ala Tyr Arg Trp Arg Leu Ser His Arg Pro
1               5                   10                  15

Lys Thr Gly

<210> SEQ ID NO 37
<211> LENGTH: 20
<212> TYPE: PRT
<213> ORGANISM: Artificial
<220> FEATURE:
<223> OTHER INFORMATION: Thrombospondin region plus N-terminal CYS

<400> SEQUENCE: 37

Cys Gly Trp Lys Asp Phe Thr Ala Tyr Arg Trp Arg Leu Ser His Arg
1               5                   10                  15

Pro Lys Thr Gly
            20

<210> SEQ ID NO 38
<211> LENGTH: 1170
<212> TYPE: PRT
<213> ORGANISM: Human

<400> SEQUENCE: 38

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
            20                  25                  30

Ile Phe Glu Leu Thr Gly Ala Ala Arg Lys Gly Ser Gly Arg Arg Leu
        35                  40                  45

Val Lys Gly Pro Asp Pro Ser Ser Pro Ala Phe Arg Ile Glu Asp Ala
    50                  55                  60

Asn Leu Ile Pro Pro Val Pro Asp Asp Lys Phe Gln Asp Leu Val Asp
65                  70                  75                  80

Ala Val Arg Ala Glu Lys Gly Phe Leu Leu Leu Ala Ser Leu Arg Gln
                85                  90                  95

Met Lys Lys Thr Arg Gly Thr Leu Leu Ala Leu Glu Arg Lys Asp His
            100                 105                 110

Ser Gly Gln Val Phe Ser Val Val Ser Asn Gly Lys Ala Gly Thr Leu
        115                 120                 125

Asp Leu Ser Leu Thr Val Gln Gly Lys Gln His Val Val Ser Val Glu
    130                 135                 140
```

-continued

```
Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
            165                 170                 175

Ala Glu Leu Asp Val Pro Ile Gln Ser Val Phe Thr Arg Asp Leu Ala
        180                 185                 190

Ser Ile Ala Arg Leu Arg Ile Ala Lys Gly Val Asn Asp Asn Phe
    195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
                260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
        290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
                340                 345                 350

Cys Pro Ile Met Pro Cys Ser Asn Ala Thr Val Pro Asp Gly Glu Cys
        355                 360                 365

Cys Pro Arg Cys Trp Pro Ser Asp Ser Ala Asp Asp Gly Trp Ser Pro
        370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
                420                 425                 430

Lys Gln Asp Gly Gly Trp Ser His Trp Ser Pro Trp Ser Ser Cys Ser
            435                 440                 445

Val Thr Cys Gly Asp Gly Val Ile Thr Arg Ile Arg Leu Cys Asn Ser
450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
            500                 505                 510

Gln Lys Arg Ser Arg Leu Cys Asn Asn Pro Ala Pro Gln Phe Gly Gly
            515                 520                 525

Lys Asp Cys Val Gly Asp Val Thr Glu Asn Gln Ile Cys Asn Lys Gln
530                 535                 540

Asp Cys Pro Ile Asp Gly Cys Leu Ser Asn Pro Cys Phe Ala Gly Val
545                 550                 555                 560
```

```
Lys Cys Thr Ser Tyr Pro Asp Gly Ser Trp Lys Cys Ala Cys Pro
                565                 570                 575

Pro Gly Tyr Ser Gly Asn Gly Ile Gln Cys Thr Asp Val Asp Glu Cys
            580                 585                 590

Lys Glu Val Pro Asp Ala Cys Phe Asn His Asn Gly Glu His Arg Cys
                595                 600                 605

Glu Asn Thr Asp Pro Gly Tyr Asn Cys Leu Pro Cys Pro Pro Arg Phe
        610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
                675                 680                 685

Cys Gly Glu Asp Thr Asp Leu Asp Gly Trp Pro Asn Glu Asn Leu Val
690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asn Asp Lys Ile Pro Asp Asp Arg Asp
                740                 745                 750

Asn Cys Pro Phe His Tyr Asn Pro Ala Gln Tyr Asp Tyr Asp Arg Asp
                755                 760                 765

Asp Val Gly Asp Arg Cys Asp Asn Cys Pro Tyr Asn His Asn Pro Asp
        770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
                820                 825                 830

Cys Asp Asn Cys Pro Leu Glu His Asn Pro Asp Gln Leu Asp Ser Asp
            835                 840                 845

Ser Asp Arg Ile Gly Asp Thr Cys Asp Asn Asn Gln Asp Ile Asp Glu
    850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
            900                 905                 910

Val Pro Asn Pro Asp Gln Lys Asp Ser Asp Gly Asp Gly Arg Gly Asp
            915                 920                 925

Ala Cys Lys Asp Asp Phe Asp His Asp Ser Val Pro Asp Ile Asp Asp
        930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
                965                 970                 975
```

```
Trp Val Val Arg His Gln Gly Lys Glu Leu Val Gln Thr Val Asn Cys
            980                 985                 990

Asp Pro Gly Leu Ala Val Gly Tyr Asp Glu Phe Asn Ala Val Asp Phe
        995                1000                1005

Ser Gly Thr Phe Phe Ile Asn Thr Glu Arg Asp Asp Tyr Ala
    1010                1015                1020

Gly Phe Val Phe Gly Tyr Gln Ser Ser Ser Arg Phe Tyr Val Val
    1025                1030                1035

Met Trp Lys Gln Val Thr Gln Ser Tyr Trp Asp Thr Asn Pro Thr
    1040                1045                1050

Arg Ala Gln Gly Tyr Ser Gly Leu Ser Val Lys Val Val Asn Ser
    1055                1060                1065

Thr Thr Gly Pro Gly Glu His Leu Arg Asn Ala Leu Trp His Thr
    1070                1075                1080

Gly Asn Thr Pro Gly Gln Val Arg Thr Leu Trp His Asp Pro Arg
    1085                1090                1095

His Ile Gly Trp Lys Asp Phe Thr Ala Tyr Arg Trp Arg Leu Ser
    1100                1105                1110

His Arg Pro Lys Thr Gly Phe Ile Arg Val Val Met Tyr Glu Gly
    1115                1120                1125

Lys Lys Ile Met Ala Asp Ser Gly Pro Ile Tyr Asp Lys Thr Tyr
    1130                1135                1140

Ala Gly Gly Arg Leu Gly Leu Phe Val Phe Ser Gln Glu Met Val
    1145                1150                1155

Phe Phe Ser Asp Leu Lys Tyr Glu Cys Arg Asp Pro
    1160                1165                1170

<210> SEQ ID NO 39
<211> LENGTH: 18
<212> TYPE: PRT
<213> ORGANISM: Artificial
<220> FEATURE:
<223> OTHER INFORMATION: Thrombospondin Region

<400> SEQUENCE: 39

Met Gly Leu Ala Trp Gly Leu Gly Val Leu Phe Leu Met His Val Cys
1               5                   10                  15

Gly Thr

<210> SEQ ID NO 40
<211> LENGTH: 240
<212> TYPE: PRT
<213> ORGANISM: Artificial
<220> FEATURE:
<223> OTHER INFORMATION: Thrombospondin Region plus N-terminal domain

<400> SEQUENCE: 40

Asn Arg Ile Pro Glu Ser Gly Gly Asp Asn Ser Val Phe Asp Ile Phe
1               5                   10                  15

Glu Leu Thr Gly Ala Ala Arg Lys Gly Ser Gly Arg Arg Leu Val Lys
            20                  25                  30

Gly Pro Asp Pro Ser Ser Pro Ala Phe Arg Ile Glu Asp Ala Asn Leu
        35                  40                  45

Ile Pro Pro Val Pro Asp Asp Lys Phe Gln Asp Leu Val Asp Ala Val
    50                  55                  60

Arg Ala Glu Lys Gly Phe Leu Leu Leu Ala Ser Leu Arg Gln Met Lys
65                  70                  75                  80
```

```
Lys Thr Arg Gly Thr Leu Leu Ala Leu Glu Arg Lys Asp His Ser Gly
                85                  90                  95

Gln Val Phe Ser Val Val Ser Asn Gly Lys Ala Gly Thr Leu Asp Leu
            100                 105                 110

Ser Leu Thr Val Gln Gly Lys Gln His Val Val Ser Val Glu Glu Ala
        115                 120                 125

Leu Leu Ala Thr Gly Gln Trp Lys Ser Ile Thr Leu Phe Val Gln Glu
130                 135                 140

Asp Arg Ala Gln Leu Tyr Ile Asp Cys Glu Lys Met Glu Asn Ala Glu
145                 150                 155                 160

Leu Asp Val Pro Ile Gln Ser Val Phe Thr Arg Asp Leu Ala Ser Ile
                165                 170                 175

Ala Arg Leu Arg Ile Ala Lys Gly Gly Val Asn Asp Asn Phe Gln Gly
            180                 185                 190

Val Leu Gln Asn Val Arg Phe Val Phe Gly Thr Thr Pro Glu Asp Ile
        195                 200                 205

Leu Arg Asn Lys Gly Cys Ser Ser Thr Ser Val Leu Leu Thr Leu
210                 215                 220

Asp Asn Asn Val Val Asn Gly Ser Ser Pro Ala Ile Arg Thr Asn Tyr
225                 230                 235                 240

<210> SEQ ID NO 41
<211> LENGTH: 22
<212> TYPE: PRT
<213> ORGANISM: Artificial
<220> FEATURE:
<223> OTHER INFORMATION: Thrombospondin region plus domain of
      inter-chain disulfide bonds

<400> SEQUENCE: 41

Ile Gly His Lys Thr Lys Asp Leu Gln Ala Ile Cys Gly Ile Ser Cys
1               5                   10                  15

Asp Glu Leu Ser Ser Met
            20

<210> SEQ ID NO 42
<211> LENGTH: 98
<212> TYPE: PRT
<213> ORGANISM: Artificial
<220> FEATURE:
<223> OTHER INFORMATION: Thrombospondin region plus procollagen homology
      domain

<400> SEQUENCE: 42

Val Leu Glu Leu Arg Gly Leu Arg Thr Ile Val Thr Thr Leu Gln Asp
1               5                   10                  15

Ser Ile Arg Lys Val Thr Glu Glu Asn Lys Glu Leu Ala Asn Glu Leu
            20                  25                  30

Arg Arg Pro Pro Leu Cys Tyr His Asn Gly Val Gln Tyr Arg Asn Asn
        35                  40                  45

Glu Glu Trp Thr Val Asp Ser Cys Thr Glu Cys His Cys Gln Asn Ser
    50                  55                  60

Val Thr Ile Cys Lys Lys Val Ser Cys Pro Ile Met Pro Cys Ser Asn
65                  70                  75                  80

Ala Thr Val Pro Asp Gly Glu Cys Cys Pro Arg Cys Trp Pro Ser Asp
                85                  90                  95

Ser Ala
```

```
<210> SEQ ID NO 43
<211> LENGTH: 170
<212> TYPE: PRT
<213> ORGANISM: Artificial
<220> FEATURE:
<223> OTHER INFORMATION: Thrombospondin region plus domain of type 1
      repeats

<400> SEQUENCE: 43

Asp Asp Gly Trp Ser Pro Trp Ser Glu Trp Thr Ser Cys Ser Thr Ser
1               5                   10                  15

Cys Gly Asn Gly Ile Gln Gln Arg Gly Arg Ser Cys Asp Ser Leu Asn
            20                  25                  30

Asn Arg Cys Glu Gly Ser Ser Val Gln Thr Arg Thr Cys His Ile Gln
        35                  40                  45

Glu Cys Asp Lys Arg Phe Lys Gln Asp Gly Gly Trp Ser His Trp Ser
    50                  55                  60

Pro Trp Ser Ser Cys Ser Val Thr Cys Gly Asp Gly Val Ile Thr Arg
65                  70                  75                  80

Ile Arg Leu Cys Asn Ser Pro Ser Pro Gln Met Asn Gly Lys Pro Cys
                85                  90                  95

Glu Gly Glu Ala Arg Glu Thr Lys Ala Cys Lys Lys Asp Ala Cys Pro
            100                 105                 110

Ile Asn Gly Gly Trp Gly Pro Trp Ser Pro Trp Asp Ile Cys Ser Val
        115                 120                 125

Thr Cys Gly Gly Gly Val Gln Lys Arg Ser Arg Leu Cys Asn Asn Pro
    130                 135                 140

Ala Pro Gln Phe Gly Gly Lys Asp Cys Val Gly Asp Val Thr Glu Asn
145                 150                 155                 160

Gln Ile Cys Asn Lys Gln Asp Cys Pro Ile
                165                 170

<210> SEQ ID NO 44
<211> LENGTH: 143
<212> TYPE: PRT
<213> ORGANISM: Artificial
<220> FEATURE:
<223> OTHER INFORMATION: Thrombospondin region plus domain of type 2
      repeats

<400> SEQUENCE: 44

Asp Gly Cys Leu Ser Asn Pro Cys Phe Ala Gly Val Lys Cys Thr Ser
1               5                   10                  15

Tyr Pro Asp Gly Ser Trp Lys Cys Gly Ala Cys Pro Pro Gly Tyr Ser
            20                  25                  30

Gly Asn Gly Ile Gln Cys Thr Asp Val Asp Glu Cys Lys Glu Val Pro
        35                  40                  45

Asp Ala Cys Phe Asn His Asn Gly Glu His Arg Cys Glu Asn Thr Asp
    50                  55                  60

Pro Gly Tyr Asn Cys Leu Pro Cys Pro Pro Arg Phe Thr Gly Ser Gln
65                  70                  75                  80

Pro Phe Gly Gln Gly Val Glu His Ala Thr Ala Asn Lys Gln Val Cys
                85                  90                  95

Lys Pro Arg Asn Pro Cys Thr Asp Gly Thr His Asp Cys Asn Lys Asn
            100                 105                 110
```

```
Ala Lys Cys Asn Tyr Leu Gly His Tyr Ser Asp Pro Met Tyr Arg Cys
        115                 120                 125

Glu Cys Lys Pro Gly Tyr Ala Gly Asn Gly Ile Ile Cys Gly Glu
    130                 135                 140

<210> SEQ ID NO 45
<211> LENGTH: 24
<212> TYPE: PRT
<213> ORGANISM: Artificial
<220> FEATURE:
<223> OTHER INFORMATION: Thrombospondin Region plus region between the
      type 2 and the type 3 repeat

<400> SEQUENCE: 45

Asp Thr Asp Leu Asp Gly Trp Pro Asn Glu Asn Leu Val Cys Val Ala
1               5                   10                  15

Asn Ala Thr Tyr His Cys Lys Lys
            20

<210> SEQ ID NO 46
<211> LENGTH: 36
<212> TYPE: PRT
<213> ORGANISM: Artificial
<220> FEATURE:
<223> OTHER INFORMATION: Thrombospondin region

<400> SEQUENCE: 46

Asp Asn Cys Pro Asn Leu Pro Asn Ser Gly Gln Glu Asp Tyr Asp Lys
1               5                   10                  15

Asp Gly Ile Gly Asp Ala Cys Asp Asp Asp Asp Asn Asp Lys Ile
            20                  25                  30

Pro Asp Asp Arg
        35

<210> SEQ ID NO 47
<211> LENGTH: 23
<212> TYPE: PRT
<213> ORGANISM: Artificial
<220> FEATURE:
<223> OTHER INFORMATION: Thrombospondin Region

<400> SEQUENCE: 47

Asp Asn Cys Pro Phe His Tyr Asn Pro Ala Gln Tyr Asp Tyr Asp Arg
1               5                   10                  15

Asp Asp Val Gly Asp Arg Cys
            20

<210> SEQ ID NO 48
<211> LENGTH: 36
<212> TYPE: PRT
<213> ORGANISM: Artificial
<220> FEATURE:
<223> OTHER INFORMATION: Thrombospondin Region

<400> SEQUENCE: 48

Asp Asn Cys Pro Tyr Asn His Asn Pro Asp Gln Ala Asp Thr Asp Asn
1               5                   10                  15

Asn Gly Glu Gly Asp Ala Cys Ala Ala Asp Ile Asp Gly Asp Gly Ile
            20                  25                  30

Leu Asn Glu Arg
        35
```

<210> SEQ ID NO 49
<211> LENGTH: 23
<212> TYPE: PRT
<213> ORGANISM: Artificial
<220> FEATURE:
<223> OTHER INFORMATION: thrombospondin region

<400> SEQUENCE: 49

Asp Asn Cys Gln Tyr Val Tyr Asn Val Asp Gln Arg Asp Thr Asp Met
1               5                   10                  15

Asp Gly Val Gly Asp Gln Cys
            20

<210> SEQ ID NO 50
<211> LENGTH: 38
<212> TYPE: PRT
<213> ORGANISM: Artificial
<220> FEATURE:
<223> OTHER INFORMATION: Thrombospondin Region

<400> SEQUENCE: 50

Asp Asn Cys Pro Leu Glu His Asn Pro Asp Gln Leu Asp Ser Asp Ser
1               5                   10                  15

Asp Arg Ile Gly Asp Thr Cys Asp Asn Asn Gln Asp Ile Asp Glu Asp
            20                  25                  30

Gly His Gln Asn Asn Leu
        35

<210> SEQ ID NO 51
<211> LENGTH: 36
<212> TYPE: PRT
<213> ORGANISM: Artificial
<220> FEATURE:
<223> OTHER INFORMATION: Thrombospondin region

<400> SEQUENCE: 51

Asp Asn Cys Pro Tyr Val Pro Asn Ala Asn Gln Ala Asp His Asp Lys
1               5                   10                  15

Asp Gly Lys Gly Asp Ala Cys Asp His Asp Asp Asn Asp Gly Ile
            20                  25                  30

Pro Asp Asp Lys
        35

<210> SEQ ID NO 52
<211> LENGTH: 36
<212> TYPE: PRT
<213> ORGANISM: Artificial
<220> FEATURE:
<223> OTHER INFORMATION: Thrombospondin region plus domain of type 3
     repeats

<400> SEQUENCE: 52

Asp Asn Cys Arg Leu Val Pro Asn Pro Asp Gln Lys Asp Ser Asp Gly
1               5                   10                  15

Asp Gly Arg Gly Asp Ala Cys Lys Asp Asp Phe Asp His Asp Ser Val
            20                  25                  30

Pro Asp Ile Asp
        35

<210> SEQ ID NO 53
<211> LENGTH: 227
<212> TYPE: PRT
<213> ORGANISM: Artificial

```
<220> FEATURE:
<223> OTHER INFORMATION: Thrombospondin Region plus C-terminal domain

<400> SEQUENCE: 53

Asp Ile Cys Pro Glu Asn Val Asp Ile Ser Glu Thr Asp Phe Arg Arg
1               5                   10                  15

Phe Gln Met Ile Pro Leu Asp Pro Lys Gly Thr Ser Gln Asn Asp Pro
            20                  25                  30

Asn Trp Val Arg His Gln Gly Lys Glu Leu Val Gln Thr Val Asn
        35                  40                  45

Cys Asp Pro Gly Leu Ala Val Gly Tyr Asp Glu Phe Asn Ala Val Asp
    50                  55                  60

Phe Ser Gly Thr Phe Phe Ile Asn Thr Glu Arg Asp Asp Tyr Ala
65              70                  75                  80

Gly Phe Val Phe Gly Tyr Gln Ser Ser Arg Phe Tyr Val Val Met
                85                  90                  95

Trp Lys Gln Val Thr Gln Ser Tyr Trp Asp Thr Asn Pro Thr Arg Ala
            100                 105                 110

Gln Gly Tyr Ser Gly Leu Ser Val Lys Val Val Asn Ser Thr Thr Gly
        115                 120                 125

Pro Gly Glu His Leu Arg Asn Ala Leu Trp His Thr Gly Asn Thr Pro
    130                 135                 140

Gly Gln Val Arg Thr Leu Trp His Asp Pro Arg His Ile Gly Trp Lys
145                 150                 155                 160

Asp Phe Thr Ala Tyr Arg Trp Arg Leu Ser His Arg Pro Lys Thr Gly
                165                 170                 175

Phe Ile Arg Val Val Met Tyr Glu Gly Lys Lys Ile Met Ala Asp Ser
            180                 185                 190

Gly Pro Ile Tyr Asp Lys Thr Tyr Ala Gly Gly Arg Leu Gly Leu Phe
        195                 200                 205

Val Phe Ser Gln Glu Met Val Phe Phe Ser Asp Leu Lys Tyr Glu Cys
    210                 215                 220

Arg Asp Pro
225

<210> SEQ ID NO 54
<211> LENGTH: 6
<212> TYPE: PRT
<213> ORGANISM: Artificial
<220> FEATURE:
<223> OTHER INFORMATION: Thrombospondin region

<400> SEQUENCE: 54

Cys Ser Val Thr Cys Gly
1               5

<210> SEQ ID NO 55
<211> LENGTH: 8
<212> TYPE: PRT
<213> ORGANISM: Artificial
<220> FEATURE:
<223> OTHER INFORMATION: Thrombospondin Region

<400> SEQUENCE: 55

Arg Phe Tyr Val Val Met Trp Lys
1               5
```

```
<210> SEQ ID NO 56
<211> LENGTH: 6
<212> TYPE: PRT
<213> ORGANISM: Artificial
<220> FEATURE:
<223> OTHER INFORMATION: Thrombospondin region

<400> SEQUENCE: 56

Arg Phe Tyr Val Val Met
1               5

<210> SEQ ID NO 57
<211> LENGTH: 7
<212> TYPE: PRT
<213> ORGANISM: Artificial
<220> FEATURE:
<223> OTHER INFORMATION: Thrombospondin Region

<400> SEQUENCE: 57

Phe Tyr Val Val Met Trp Lys
1               5

<210> SEQ ID NO 58
<211> LENGTH: 5
<212> TYPE: PRT
<213> ORGANISM: Artificial
<220> FEATURE:
<223> OTHER INFORMATION: Thrombospondin Region

<400> SEQUENCE: 58

Ile Arg Val Val Met
1               5

<210> SEQ ID NO 59
<211> LENGTH: 10
<212> TYPE: PRT
<213> ORGANISM: Artificial
<220> FEATURE:
<223> OTHER INFORMATION: Thrombospondin Region

<400> SEQUENCE: 59

Arg Lys Gly Ser Gly Arg Arg Leu Val Lys
1               5                   10

<210> SEQ ID NO 60
<211> LENGTH: 7
<212> TYPE: PRT
<213> ORGANISM: Artificial
<220> FEATURE:
<223> OTHER INFORMATION: thrombospondin Region

<400> SEQUENCE: 60

Arg Lys Gly Ser Gly Arg Arg
1               5

<210> SEQ ID NO 61
<211> LENGTH: 7
<212> TYPE: PRT
<213> ORGANISM: Artificial
<220> FEATURE:
<223> OTHER INFORMATION: Thrombospondin region

<400> SEQUENCE: 61

Arg Gln Met Lys Lys Thr Arg
1               5
```

-continued

```
<210> SEQ ID NO 62
<211> LENGTH: 8
<212> TYPE: PRT
<213> ORGANISM: Artificial
<220> FEATURE:
<223> OTHER INFORMATION: Thrombospondin Region

<400> SEQUENCE: 62

Ala Arg Lys Gly Ser Gly Arg Arg
1               5

<210> SEQ ID NO 63
<211> LENGTH: 6
<212> TYPE: PRT
<213> ORGANISM: Artificial
<220> FEATURE:
<223> OTHER INFORMATION: Thrombospondin Region

<400> SEQUENCE: 63

Met Lys Lys Thr Arg Gly
1               5

<210> SEQ ID NO 64
<211> LENGTH: 12
<212> TYPE: PRT
<213> ORGANISM: Artificial
<220> FEATURE:
<223> OTHER INFORMATION: Thrombospondin Region

<400> SEQUENCE: 64

Arg Leu Arg Ile Ala Lys Gly Gly Val Asn Asp Asn
1               5                   10
```